United States Patent [19]

Mizuno et al.

[11] Patent Number: 5,399,557
[45] Date of Patent: Mar. 21, 1995

[54] PYRROLOAZEPINE COMPOUND

[75] Inventors: Akira Mizuno, Kyoto; Mikiko Miya, Tsukuba; Norio Inomata, Mino; Toshio Tatsuoka, Nishinomiya; Takafumi Ishihara, Takatsuki, all of Japan

[73] Assignee: Suntory Limited, Osaka, Japan

[21] Appl. No.: 30,427

[22] PCT Filed: Aug. 6, 1992

[86] PCT No.: PCT/JP92/01009
§ 371 Date: Apr. 7, 1993
§ 102(e) Date: Apr. 7, 1993

[87] PCT Pub. No.: WO93/03032
PCT Pub. Date: Feb. 18, 1993

[30] Foreign Application Priority Data

Aug. 7, 1991 [JP] Japan .................. 3-221192

[51] Int. Cl.⁶ .................. A61K 31/55; C07D 487/04
[52] U.S. Cl. .................. 514/215; 540/526; 540/527; 540/580; 540/521
[58] Field of Search ............ 540/526, 527, 580, 521; 514/215

[56] References Cited

U.S. PATENT DOCUMENTS 3,563,979 2/1971 Hester, Jr. .
3,573,323 3/1971 Hester, Jr. .
3,573,324 3/1971 Hester, Jr. .
5,206,239 4/1993 Mizuno et al. .

FOREIGN PATENT DOCUMENTS 62-161786 7/1987 Japan .
2-500738 3/1990 Japan .
WO87/07274 12/1987 WIPO .

OTHER PUBLICATIONS

Aust. J. Chem., vol. 43, 1990, pp. 355–365, B. Kasum, et al., "Dihydroindol-7(6H)-Ones and 6,7-Dihydropyrrolo[2,3-C]Azepine-4,8(1H,5H)-Dione".
Chemical Abstracts, vol. 102, 1985, AN-146334h, N. K. Utkina, et al., "Nitrogen-Containing Metabolites of the Marine Sponge Acanthella Carteri".
Tetrahedron, vol. 41, No. 24, pp. 6019–6033, 1985, G.

De Nanteuil, et al., "Invertebres Marins Du Lagon Neo-Caledonien-V1", (With English Abstract).
Journal of The Chemical Society, pp. 435 & 436, Jan. 3, 1980, G. Sharm, et al., "Characterization of a Yellow Compound Isolated from the Marine Sponge Phakellia Flabellata".
Journal of Natural Products, vol. 48, No. 1, pp. 47–53 (1985).

*Primary Examiner*—Mukund J. Shah
*Assistant Examiner*—Matthew V. Grumbling
*Attorney, Agent, or Firm*—Oblon, Spivak, McClelland, Maier & Neustadt

[57] ABSTRACT

This invention provides a pyrroloazepine compound represented by the following formula (I) or (II):

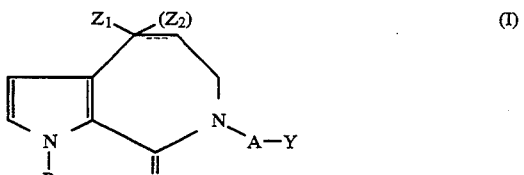

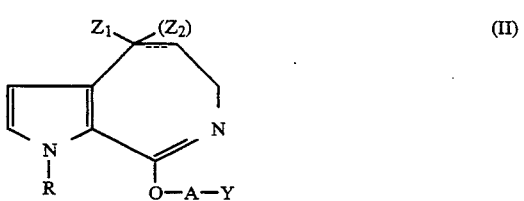

wherein $Z_1$, $Z_2$, R, A and Y are defined in the claims.

The pyrroloazepine compounds according to the present invention are drugs having excellent anti-serotonin action. Coupled with their high safety, they can therefore be used as novel therapeutics for ischemic heart diseases. In addition, the compounds of the present invention include those having anti-$\alpha_1$ action. Such compounds are effective as hypotensive drugs. Pyrroloazepine compounds according to the present invention are therefore extremely useful as therapeutics for a wide variety of circulatory diseases.

7 Claims, No Drawings

PYRROLOAZEPINE COMPOUND

TECHNICAL FIELD

The present invention relates to novel pyrroloazepine compounds, and more specifically to novel pyrroloazepine compounds and salts thereof, said compounds and salts being useful as therapeutics for circulatory diseases such as ischemic heart diseases and hypertension, their preparation processes and therapeutics for circulatory diseases, said therapeutics containing them as active ingredients.

BACKGROUND ART

It is known that serotonin is contained abundantly in platelets, a blood component, and that upon stimulation by thromboxane $A_2$, ADP, collagen or the like, it is released to synergistically act on the release of various platelet aggregation factors through activation of the serotonin-2 receptor in platelets and vascular smooth muscle cells and on vasoconstriction by norepinephrine through the $\alpha_1$ receptor, thereby inducing strong platelet aggregation and vasoconstriction [P. M. Vanhoutte, "Journal of Cardiovascular Pharmacology", Vol. 17 (Supple. 5), S6-S12 (1991)].

With the foregoing in view, there is hence an outstanding desire for the development of a serotonin-2 receptor antagonist as a circulatory disease therapeutic for preventing thrombus formation and vasoconstriction so that the serotonin-2 receptor antagonist can be used for hypertension and ischemic heart diseases such as angina pectoris, myocardial infarction, heart failure and post-PTCA restenosis. It is however the present situation that no drug has been obtained yet with sufficient antagonism and selectivity. Pharmaceuticals having $\alpha_1$-blocking action in combination with anti-serotonin action are expected to reduce side effects caused by hypotensive action based on $\alpha_1$-blocking action, such as orthostatic disorder and reflex tachycardia, so that some drugs having both actions have been developed. However, none of them have been provided with sufficient hypotensive action.

DISCLOSURE OF THE INVENTION

In view of the foregoing circumstances, the present inventors have carried out an extensive investigation, resulting in the finding of certain pyrroloazepine compounds which have strong anti-serotonin action without significant side effects and toxicity and are useful as therapeutics for ischemic heart diseases based on their antagonism against serotonin receptors. Some of the compounds according to the present invention have also been found to have $\alpha_1$-blocking action too, whereby they are useful as hypotensive drugs with reduced side effects and can be used in a wide variety of therapeutics for circulatory diseases.

The present invention has been completed based on the above described findings and provides a pyrroloazepine compound represented by the following formula (I) or (II):

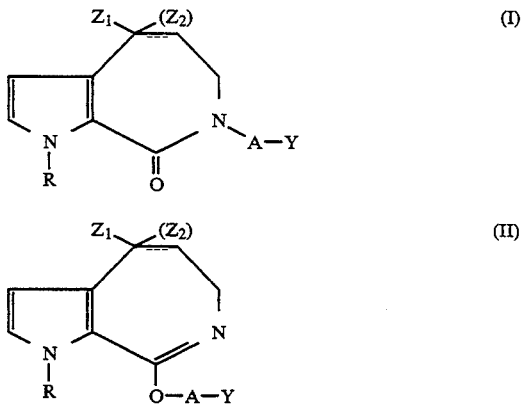

wherein the dashed line indicates the presence or absence of a bond and when the bond indicated by the dashed line is present, $Z_1$ represents a hydrogen atom but, when the bond indicated by the dashed line is absent, $Z_1$ represents a hydrogen atom and $Z_2$ represents a hydroxyl group or $Z_1$ and $Z_2$ are taken together to form an oxygen atom or a group $NOR_1$, in which $R_1$ represents a hydrogen atom, an alkyl group, a substituted or unsubstituted aryl group or a substituted or unsubstituted aralkyl group; R represents an alkyl group, a cycloalkyl group, a cycloalkyl-alkyl group, a substituted or unsubstituted aryl group, or a substituted or unsubstituted aralkyl group; A represents an alkylene, alkenylene or alkynylene group; and Y represents a substituted or unsubstituted heterocyclic group or a group:

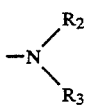

in which $R_2$ and $R_3$ may be the same or different and individually represent a hydrogen atom, an alkyl group which may be substituted by a lower alkoxy group or a substituted or unsubstituted aryloxy group, a substituted or unsubstituted aryl group or a substituted or unsubstituted aralkyl group; or a salt thereof; a preparation process thereof; and a therapeutic for circulatory diseases, said therapeutic containing as an active ingredient the pyrroloazepine compound or the salt thereof.

BEST MODES FOR CARRYING OUT THE INVENTION

In the pyrroloazepine compounds (I) and (II) of the present invention, preferred examples of group R include branched or linear $C_{1-8}$ alkyl groups such as methyl, ethyl, n-propyl, isopropyl and n-pentyl; $C_{3-8}$ cyclolalkyl groups such as cyclopropyl, cyclopentyl and cyclohexyl; $C_{3-8}$ cycloalkyl-alkyl groups such as cyclopropylmethyl, cyclohexylmethyl and cyclohexylethyl; aryl groups such as phenyl, phenyl substituted by one or more halogen atoms such as fluorine, chlorine and bromine, $C_{1-4}$ alkyl groups such as methyl and ethyl and/or $C_{1-4}$ alkoxy groups such as methoxy and ethoxy, and naphthyl; and aralkyl groups such as diphenylmethyl, benzyl and phenethyl. In this case, each aromatic ring may be substituted by one or more of the halogen atoms, alkyl groups and/or alkoxy groups referred to above. Among them, methyl, ethyl and benzyl groups are particularly preferred.

In addition, preferred examples of group A include branched or linear $C_{2-10}$ alkylene groups such as ethylene, trimethylene, tetramethylene, pentamethylene, 3,3-dimethylpentamethylene and octamethylene; branched or linear $C_{4-10}$ alkenylene groups such as 2-butenylene and 3-pentenylene; and branched or linear $C_{4-10}$ alkynylene groups such as 2-butynylene and 3-pentynylene. Among them, trimethylene, tetramethylene and pentamethylene groups are particularly preferred.

Further, preferred examples concerning groups $Z_1$ and $Z_2$ include that inducing no bond indicated by the dashed line and containing a hydrogen atom as $Z_1$ and a hydroxyl group as $Z_2$ and those where $Z_1$ and $Z_2$ are taken together to form an oxygen atom or a group —$NOR_1$.

Preferred examples of $R_1$ in the group —$NOR_1$ include a hydrogen atom; branched or linear $C_{3-8}$ alkyl groups such as methyl, ethyl and isopropyl; aryl groups such as phenyl and phenyl substituted by one or more of the halogen atoms, alkyl groups and/or alkoxy groups referred to above; and aralkyl groups such as benzyl and diphenylmethyl. In this case, each aromatic ring may be substituted by one or more of the halogen atoms, alkyl groups and/or alkoxy groups referred to above. Among these, a hydrogen atom and a methyl group are particularly preferred.

Furthermore, preferred examples of group —Y include groups represented by the following formula:

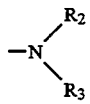

in which $R_2$ and $R_3$ may be the same or different and individually represent a hydrogen atom, a lower alkyl group such as methyl, ethyl and n-propyl, an alkyl group which is substituted by a lower alkoxy group or a substituted or unsubstituted aryloxy group such as 3-methoxypropyl, 2-phenoxyethyl and 2-(2-methoxyphenyloxy)ethyl, a substituted or unsubstituted aryl group such as phenyl and 2-methoxyphenyl and a substituted or unsubstituted aralkyl group such as 2-(3,4-dimethoxyphenyl)ethyl; and a heterocyclic group led by a monovalent group derived from piperazine, homopiperazine, piperidine or imidazole. These heterocyclic groups may be substituted. The following heterocyclic groups can be given as more preferred examples.

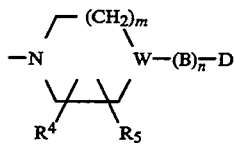

wherein $R_4$ and $R_5$ individually represent a hydrogen atom or a branched or linear alkyl group, preferably a hydrogen atom or a lower alkyl group such as a methyl or ethyl group, when W represents C—$R_6$ ($R_6$ is preferably a hydrogen atom or a $C_{1-4}$ alkyl group such as a methyl and ethyl group with a hydrogen atom being particularly preferred), m stands for 0, 1 or 2 with 1 being preferred, B represents an oxygen atom, a sulfur atom, a carbonyl group, a sulfinyl group, a sulfonyl group, an alkylene group (preferably a methylene group), alkenylene group (preferably 2-propenylene group), a substituted or unsubstituted phenylmethylene group, a substituted or unsubstituted hydroxymethylene group, a substituted or unsubstituted, cyclic or non-cyclic acetal group, with a carbonyl group being particularly preferred. Examples of the cyclic and non-cyclic acetal, which may be substituted or unsubstituted, include:

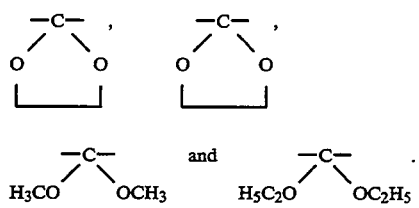

When W represents a nitrogen atom, m stands for 1 or 2, with 1 being more preferred, and B represents a carbonyl group, a sulfonyl group, an alkylene group (preferably, a methylene group), an alkenylene group (preferably a 2-propenylene group) and a substituted or unsubstituted phenylmethylene group.

In addition, n stands for 0 or 1 and D represents a substituted or unsubstituted aryl group or a substituted or unsubstituted aromatic heterocyclic group, preferably a phenyl group, a phenyl group substituted by one or more of the halogen atoms, alkyl groups and/or alkoxy groups referred to above, a pyrimidinyl group, a pyridyl group, a benzisothiazolyl group, a benzisoxazolyl group or a furyl group, with a phenyl group or a halogen- or alkoxy-substituted phenyl group being preferred.

Many of the compounds (I) and (II) according to the present invention have isomers. It is to be noted that these isomers are all embraced by the present invention. For example, when there is a hydroxyimino group or an O-substituted hydroxyimino group at 4-position of the pyrroloazepine ring, there are both an (E)-isomer and a (Z)-isomer with respect to the group. The compounds of the present invention also include these individual isomers and their mixtures.

Various processes can be employed for the preparation of the pyrroloazepine compounds (I) and (II) according to the present invention. It is however preferable to prepare the pyrroloazepine compounds (I) and (II), for example, by any of the following processes.

Process 1:

Among the pyrroloazepine compounds (I) and (II), each of compounds (Ia) and (IIa) in which $Z_1$ and $Z_2$ are taken together to form an oxygen atom can be obtained in accordance with the following reaction scheme, namely, by converting the compound represented by formula (III) to the compound represented by formula (V) and then reacting the compound (V) with the nitrogen-containing compound represented by formula (VI) or a salt thereof.

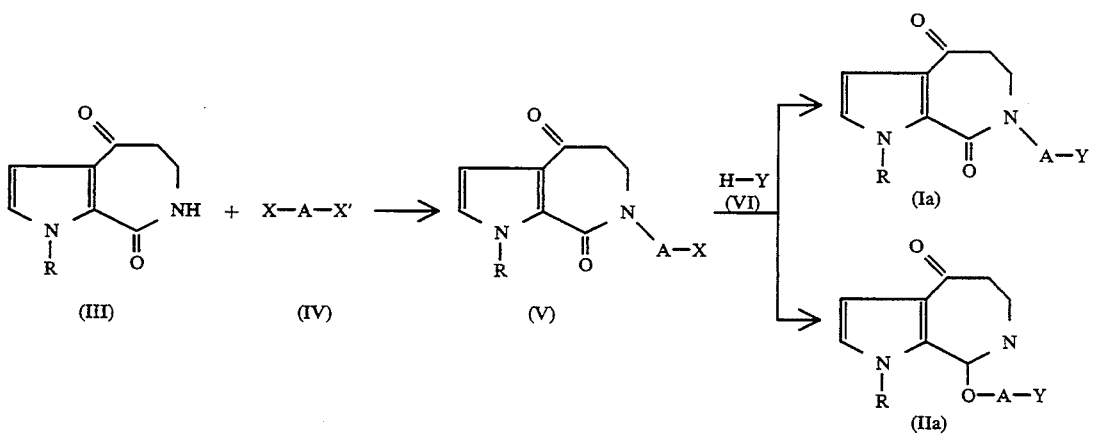

wherein A, R and Y have the same meanings as defined above, X and X' may be the same or different and individually represents a substituent easily replaceable with an amino group.

The conversion from the compound (III) to the compound (V) can be effected by treating the compound (III) with an organic or inorganic base and then reacting with the compound (IV) or by causing the compound (IV) to act on the compound (III) in the presence of such a base.

Examples of the substituent, which is easily replaceable with an amino group, as each of the groups X and X' in the compound (IV) include halogen atoms such as chlorine and bromine, alkylsulfonyloxy groups such as methanesulfonyloxy, and arylsulfonyloxy groups such as p-toluenesulfonyloxy. Further, exemplary organic or inorganic bases include sodium hydride, potassium hydride, n-butyl lithium, potassium t-butoxide and the like. Illustrative solvents usable in the present reaction include ether, tetrahydrofuran, dioxane, dimethylformamide, N-methylpyrrolidone, dimethyl sulfoxide and the like. The reaction may be conducted at −20° C. to reflux temperature.

To prepare the compound (Ia) and (IIa) by reacting the compound (V) with the nitrogen-containing compound (VI), it is only necessary to react the nitrogen-containing compound (VI) or an organic acid or inorganic acid salt thereof with the compound (V), optionally together with an organic base such as triethylamine, pyridine, collidine, 1,8-diazabicyclo-[5.4.0]undec-7-ene (DBU) or potassium t-butoxide or an inorganic base such as potassium carbonate, sodium carbonate, potassium hydroxide, sodium hydroxide or sodium hydride, optionally after addition of an iodide such as sodium iodide or potassium iodide at 0°–150° C. in the above solvent or in a solvent such as methanol, ethanol, propanol or butanol.

In the above reaction, it is possible to change the respective production ratios of the compound (Ia) and (IIa) by altering their reaction conditions. The ratio of the compound (Ia) can be raised substantially, for example, by the addition of sodium iodide upon reaction.

Examples of the nitrogen-containing compound (VI) include dimethylamine, isopropylamine, t-butylamine, 3-phenylpropylamine, 2-phenoxyethylamine, N-methyl-3,4-dimethoxyphenethylamine, N-propyl-2-(8-hydroxy-1,2,3,4-tetrahydronaphthyl)amine, 1-ethoxycarbonylpiperazine, 1-phenylpiperazine, 1-(2-methoxyphenyl)piperazine, 1-(3-methoxyphenyl)piperazine, 1-(4-methoxyphenyl)piperazine, 1-(2-chlorophenyl)piperazine, 1-(3-chlorophenyl)piperazine, 1-(4-chlorophenyl)piperazine, 1-(4-fluorophenyl)piperazine, 1-(2-pyridyl)piperazine, 1-(2-pyrimidyl)piperazine, 1-benzylpiperazine, 1-diphenylmethylpiperazine, 1-cinnamylpiperazine, 1-(1,4-benzodioxan-2-ylmethyl)piperazine, 1-benzoylpiperazine, 1-(4-benzyloxybenzoyl)piperazine, 1-(4-hydroxybenzoyl)piperazine, 2-furoylpiperazine, 4-phenylpiperidine, 4-benzylpiperidine, α,α-bis(4-fluorophenyl)-4-piperidinemethanol, 4-(diphenylmethoxy)piperidine, 4-(4-fluorobenzoyl)piperidine, 4-benzoylpiperidine, 4-(4-methoxybenzoyl)piperidine, 4-(4-chlorobenzoyl)piperidine, 3-(4-fluorobenzoyl)piperidine, 3-benzoylpyrrolidine, 3-(4-fluorobenzoyl)pyrrolidine, 4-(4-fluorophenoxy)piperidine, 4-[(4-fluorophenyl)thio]piperidine, 4-[(4-fluorophenyl)sulfinyl]piperidine, 4-[(4-fluorophenyl)sulfonyl]piperidine, 4-(4-fluorobenzoyl)piperidine ethylene acetal, imidazole and the like. They are all either known compounds or compounds which can be readily prepared by a known process or a process similar to the known process.

Incidentally, the compounds (III) employed as starting materials in the above reaction are novel compounds. They can each be prepared, for example, in accordance with the following reaction scheme, namely, by reacting a 1-substituted pyrrole-2-carboxylic acid or a derivative thereof represented by the formula (X) with β-alanine or a derivative thereof represented by the formula (XI) or with an organic or inorganic salt of the β-alanine or the derivative thereof and optionally removing any protecting group, thereby obtaining a compound represented by the formula (XII) and then subjecting this compound to ring closure.

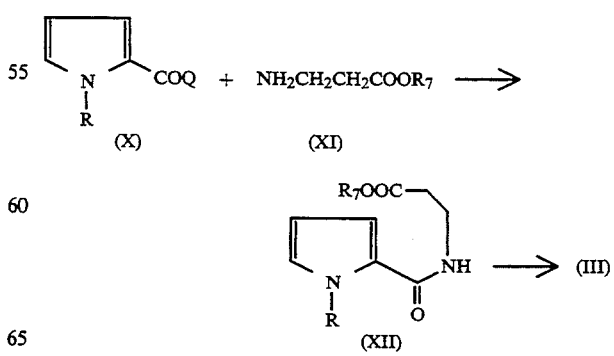

wherein R has the same meaning as defined above, $R_7$ represents a hydrogen atom or a carboxyl-protecting group, and Q represents a hydroxyl group or a substituent easily replaceable with an amino group.

Examples of the substituent easily replaceable with an amino group as represented by Q in the compound (X) include halogen atoms, carboxylic acid residue and the like. On the other hand, as the carboxyl-protecting group of the group $R_7$ in the compound (XI), it is possible to use, in addition to lower alkyl groups such as methyl, ethyl, n-propyl, isopropyl, n-butyl, isobutyl and t-butyl and $C_{7-20}$ aralkyl groups such as benzyl and 9-anthrylmethyl, the conventional protecting groups described by T. W. Greene in "Protective Groups in Organic Synthesis" (John Wiley & Sons, Inc.) and the like.

For the synthesis of the compounds (XII), it is possible to use any one of the various processes described in "Compendium of Organic Synthetic Methods" (WILEY-INTERSCIENCE; A Division of John Wiley & Sons, Inc.) and the like.

Illustrative processes include the process in which the 1-substituted pyrrole-2-carboxylic acid (the compound (X) in which Q is OH) and the compound (XI), which is β-alanine or a derivative thereof, or an organic or inorganic salt thereof, are treated with an organic compound such as diethyl phosphoryl cyanide (DEPC), diphenylphosphoryl azide (DPPA), dicyclohexylcarbodiimide (DCC), 1-ethyl-3-(3-dimethylaminopropyl)Carbodiimide hydrochloride or 2-iodo-1-methylpyridinium iodide or an inorganic compound such as silicon tetrachloride or tin tetrachloride, if necessary, in the presence of an organic or inorganic base; and the process in which the 1-substituted pyrrole-2-carboxylic acid is converted to an acid halide, a symmetric acid anhydride, a mixed acid anhydride, an active ester such as the p-nitrophenyl ester, or the like by a method known per se in the art and the compound so converted is then reacted with the compound (XI), if necessary, in the presence of an organic or inorganic base.

Each compound (XII) thus obtained is subjected to a cyclization reaction, optionally after removing the protecting group by virtue of a suitable method such as the action of an acid or a base, or catalytic reduction.

This cyclization reaction is conducted by treating the compound (XII) together with an organic acid such as methanesulfonic acid, an inorganic acid such as sulfuric acid or polyphosphoric acid or a mixture of such an organic or inorganic acid and phosphorus pentoxide at room temperature to 170° C., preferably at 80°–120° C.

In this case, a solvent which does not take part in the reaction may be added as needed. As an alternative, the cyclization reaction can also be practiced by, optionally after addition of a catalyst, treating the compound (XII) with oxalyl chloride, thionyl chloride, thionyl bromide, oxalyl bromide, phosgene, phosphorus trichloride, phosphorus tribromide, phosphoryl chloride, phosphoryl bromide or the like to convert the compound (XII) to its corresponding acid halide and then treating the acid halide at −20° C. to reflux temperature in the presence of a Lewis acid such as aluminum chloride, aluminum bromide, boron trifluoride-ether complex or tin tetrachloride in a solvent such as dichloromethane, 1,2-dichloroethane or nitromethane or heating the acid halide in acetic acid.

The compounds (III) obtained in the above manner can be used directly as starting materials for the preparation of the compounds (I) or compound (II) of the present invention. They can also be used after purification by a conventional purification method, for example, by recrystallization or column chromatography if necessary.

Process 2:

Among the pyrroloazepine compounds (I), each compound (Ia) in which $Z_1$ and $Z_2$ are taken together to form an oxygen atom can be obtained by reacting the compound represented by the formula (III) with a nitrogen-containing compound represented by formula (VII) or a salt thereof in accordance with the following reaction scheme.

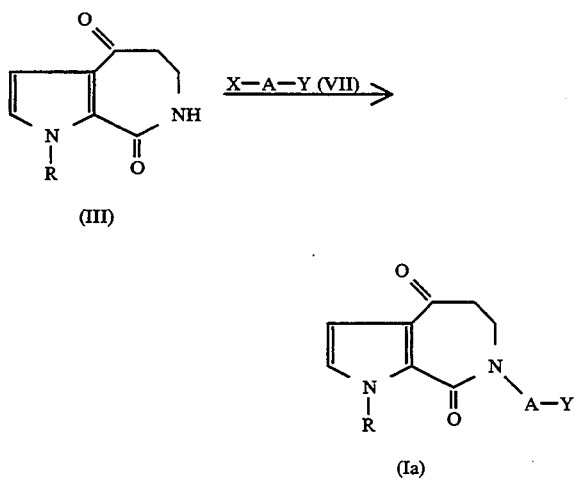

wherein A, R, X and Y have the same meanings as defined above. The conversion from the compound (III) to the compound (Ia) can be effected under the conditions similar to those shown in the conversion from the compound (III) to the compound (V) in Process 1.

Process 3:

Among the pyrroloazepine compounds (I), each compound pound (Ib) in which $Z_1$ and $Z_2$ are taken together to form a group $NOR_1$ can be prepared in accordance with the following reaction scheme, namely, (i) by causing a hydroxylamine or a derivative thereof represented by the formula (VIII) or a salt thereof to act on the compound (Ia) obtained by the above-described reaction or (ii) by causing the hydroxylamine or its derivative (VIII) or a salt thereof to act on the compound (V) and then causing a nitrogen-containing compound (VI) or a salt thereof to act further.

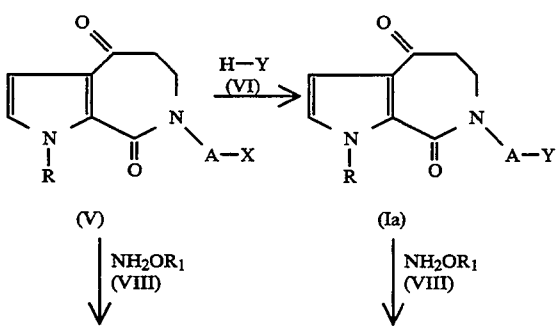

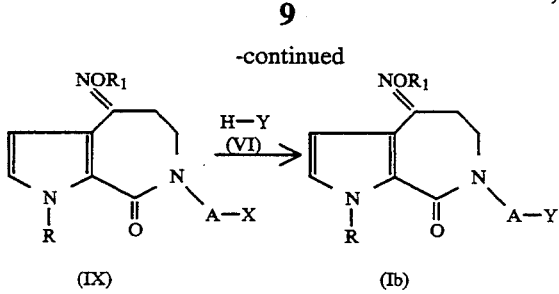

wherein A, R, $R_1$, X and Y have the same meanings as defined above.

The reaction between the above compound (Ia) or (V) and either the hydroxylamine or its derivative (VIII) can be practiced, if necessary, in the presence of an organic base such as pyridine, triethylamine, collidine, DBU or sodium acetate or an inorganic base such as potassium carbonate or sodium hydroxide. The hydroxylamine or its derivative (VIII) may also be used in the form of an organic acid salt or an inorganic acid salt.

The reaction can be conducted at 0° C. to reflux temperature, preferably 0° C.-100° C., optionally in a suitable solvent such as methanol, ethanol, propanol, tetrahydrofuran, dimethylformamide or dimethylsulfoxide.

The compound (IX) obtained by the reaction of the compound (V) with the compound (VIII) can be reacted further with the nitrogen-containing compound (VI) by the method described in Process 1, whereby the compound (V) can be converted to the compound (Ib).

Upon preparation of the compound (Ib), it is determined depending on the structure and properties of the nitrogen-containing compound (VI) whether the hydroxylamine or its derivative (VIII) should be reacted to the compound (V) or to the compound (Ia).

Where there is a group reactive to the hydroxylamine or its derivative (VIII), such as a carbonyl group, in the nitrogen-containing compound (VI), it is desirable to choose the process that the hydroxylamine or its derivative (VIII) is reacted to the compound (V).

Among the pyrroloazepine compounds (II), each compound (IIb) in which $Z_1$ and $Z_2$ are taken together to form a group $NOR_1$ can be prepared following the following reaction formula in exactly the same manner as that described above.

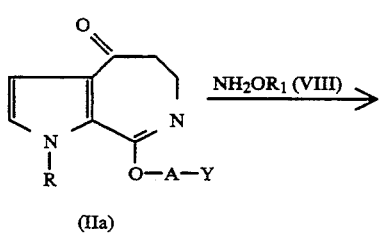

wherein A, R and $R_1$ and Y have the same meanings as defined above.

Process 4:

Among the pyrroloazepine compounds (I) and (II), compounds (Ic) and (IIc) in which $Z_1$ represents a hydrogen atom and $Z_2$ represents a hydroxyl group can be prepared by reducing the compounds (Ia) and (IIa), which have been obtained following the above reaction formula, respectively, in accordance with the following reaction formula.

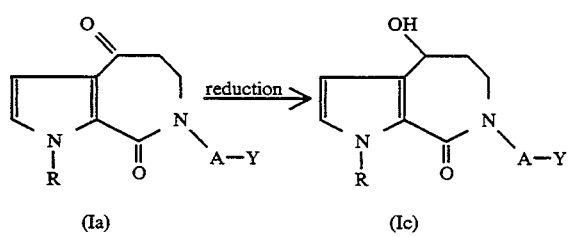

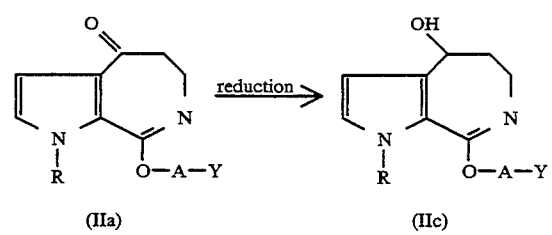

wherein A, R and Y have the same meanings as defined above.

The above reaction can be effected by reducing the compound represented by formula (Ia) or (IIa) with a reducing agent such as sodium borohydride, potassium borohydride, sodium cyanoborohydride or tri-n-butyltin hydride, in a solvent used commonly, at −78° C. to reflux temperature, preferably at −20° C. to room temperature.

The conversion from the compounds (Ia) and (IIa) to the compounds (Ic) and (IIc), respectively, can also be effected by catalytic reduction which uses Raney nickel or the like.

Process 5:

Among the pyrroloazepine compounds (I) and (II), compounds (Id) and (IId) in which the bond indicated by a dashed line exists, namely, a double bond exists and $Z_1$ represents a hydrogen atom can be prepared by subjecting the compounds (Ic) and (IIc), which have been obtained by the above reaction, respectively, to dehydration in accordance with the following reaction formula.

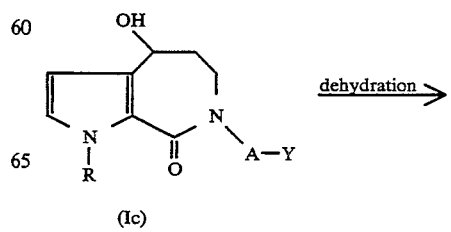

-continued

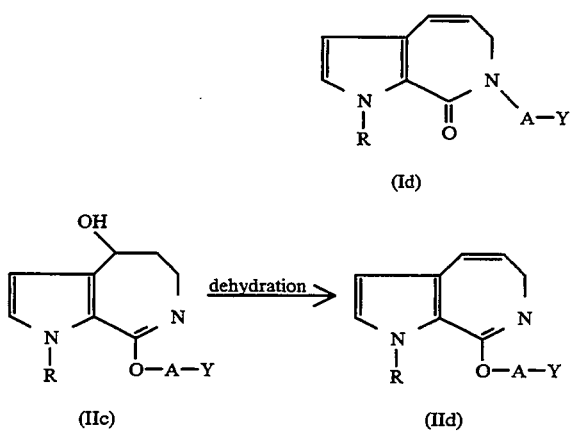

wherein A, R and Y have the same meanings as defined above.

The above reaction can be conducted by treating the compound (Ic) or (IIc) together with an acid such as hydrogen chloride, hydrogen bromide, sulfuric acid, methanesulfonic acid or p-toluenesulfonic acid optionally in a solvent such as water, methanol, ethanol, chloroform, toluene or ethyl acetate, at −20° C. to 100° C., preferably at −20° C. to room temperature.

As an alternative, the conversion from the compound represented by the formula (Ic) or (IIc) to the compound (Id) or (IId) can be effected by causing methanesulfonyl chloride, p-toluenesulfonyl chloride, phosphorus trichloride, phosphorus oxychloride, thionyl chloride or the like and a base such as triethylamine, collidine or pyridine to act on the compound (Ic) or (IIc), if necessary in a solvent such as dichloromethane, chloroform or toluene.

If necessary, the compounds (I) and (II) of the present invention obtained as described above can be reacted with various acids to convert the compounds (I) and (II) to their salts, followed by purification by a method such as recrystallization or column chromatography.

Exemplary acids usable to convert the pyrroloazepine compounds (I) and (II) to their salts include inorganic acids such as hydrochloric acid, nitric acid, sulfuric acid, phosphoric acid and hydrobromic acid; and organic acids such as maleic acid, fumaric acid, tartaric acid, lactic acid, citric acid, acetic acid, methanesulfonic acid, p-toluenesulfonic acid, adipic acid, palmitic acid and tannic acid.

The pyrroloazepine compounds (I) and (II) and their salts according to the present invention, which are obtained as described above, have anti-serotonin action and anti-$\alpha_1$ action as will be demonstrated later by tests. Further, as a result of a toxicity test, they have been found to feature high safety. The compounds according to the present invention can therefore be used as therapeutics for circulatory diseases such as ischemic heart diseases and hypertension.

When the pyrroloazepine compounds (I) or (II) according to this invention are used as drugs, they can be administered in an effective dose as they are. As an alternative, they can also be formulated into various preparation forms by known methods and then administered.

Exemplary preparation forms as drugs include orally administrable preparation forms such as tablets, powders, granules, capsules and syrups as well as parenterally administrable preparation forms such as injections and suppositories. Whichever preparation form is used, a known liquid or solid extender or carrier usable for the formulation of the preparation form can be employed.

Examples of such extender or carrier include polyvinylpyrrolidone, arabic gum, gelatin, sorbit, cyclodextrin, tragacanth gum, magnesium stearate, talc, polyethylene glycol, polyvinyl alcohol, silica, lactose, crystalline cellulose, sugar, starch, calcium phosphate, vegetable oil, carboxymethylcellulose, sodium laurylsulfate, water, ethanol, glycerin, mannitol syrup, and the like.

When the compounds according to the present invention are used as drugs, their dose varies depending on the administration purpose, the age, body weight and conditions of the patient to be administered, etc. In oral administration, the daily dose may generally be about 0.1–1,000 mg.

The present invention will next be described in further detail by the following examples and tests. But the present invention is not limited to the following examples and tests.

EXAMPLE 1

Synthesis of benzyl 3-[2-(1-methylpyrrole)carboxamido]propionate (Compound No. 1)

A solution of 72.86 g (720 mmol) of triethylamine in 100 ml of dimethylformamide (DMF) was gradually added under cooling and stirring to a solution of 37.54 g (300 mmol) of 1-methyl-2-pyrrolecarboxylic acid, 126.51 g (360 mmol) of β-alanine benzyl ester tosylate and 58.76 g (360 mmol) of diethyl cyanophophonate in 400 ml of DMF. The resulting solution was stirred at room temperature for 15 hours. The reaction mixture was concentrated under reduced pressure, followed by the addition of 1 l of a 3:1 v/v mixed solvent of ethyl acetate and benzene. The organic layer was washed successively with a saturated aqueous solution of potassium carbonate, water, 5% hydrochloric acid, water and saturated saline, followed by drying over anhydrous sodium sulfate. The solvent was distilled off under reduced pressure and the resultant oil was crystallized from hexane. The crystals so obtained were washed with hexane and then recrystallized from ethyl acetate-isopropyl ether, whereby 68.60 g of the title compound were obtained (yield: 80%).

Appearance: Colorless needle crystals. Melting point: 61.0°–62.0° C.

EXAMPLE 2

Compound Nos. 2 and 3 were obtained using 1-ethyl-2-pyrrolecarboxylic acid and 1-benzyl-2-pyrrolecarboxylic acid, respectively, in place of 1-methyl-2-pyrrolecarboxylic acid in the procedure of Example 1.

(Compound No. 2)

Benzyl 3-[2-(1-ethylpyrrole)carboxamido]propionate (Compound No. 3)

Benzyl 3-[2-(1-benzylpyrrole)carboxamido]propionate

EXAMPLE 3

Synthesis of 3-[2-(1-methylpyrrole)carboxamido]propionic acid (Compound 4)

A suspension of 27.78 g (97 mmol) of Compound No. 1 obtained in Example 1 and 2.78 g of 5% palladium-carbon in 350 ml of tetrahydrofuran (THF) was vigorously stirred under a hydrogen stream (at atmospheric pressure). After the full consumption of the starting material was confirmed by thin layer chromatography on silica gel, the reaction mixture was filtered and an insoluble matter was washed with THF. The filtrate and the washing were combined and then concentrated under reduced pressure, whereby 18.96 g of the title compound were obtained (yield: 99%).

Although this compound was sufficiently pure, it can be recrystallized from chloroform-hexane as needed.

Appearance: Colorless needle crystals. Melting point: 135.0°–137.0° C.

EXAMPLE 4

Compound Nos. 5 and 6 were obtained using Compound Nos. 2 and 3, respectively, in place of Compound 1 in the procedure of Example 3.

(Compound No. 5)

3-[2-(1-Ethylpyrrole)carboxamido]propionic acid (Compound No. 6)

3-[2-(1-Benzylpyrrole)carboxamido]propionic acid

EXAMPLE 5

Synthesis of 1-methyl-6,7-dihydropyrrolo[2,3-c]azepine-4,8(1H,5H)-dione (Compound No. 7)

A mixture of 28.0 g (143 mmol) of Compound No. 4 obtained in Example 3 and 1,000 g of polyphosphoric acid (80%) was vigorously stirred for 30 minutes at 100° C. The reaction mixture was poured into 2 l of ice water. The water layer was saturated with sodium chloride, followed by extraction with chloroform. The chloroform layer was washed with a saturated aqueous solution of sodium chloride, dried over anhydrous sodium sulfate, and then concentrated under reduced pressure.

Crude crystals so obtained were purified by chromatography on an alumina column in which "Art. 1097" (product of Merck & Co.) was used as active alumina (eluent: 3% methanol-chloroform)., whereby 17.1 g of the title compound were obtained (yield: 67%).

Although this compound was sufficiently pure, it can be recrystallized from acetonitrile as needed.

EXAMPLE 6

Compound Nos. 8 and 9 were obtained using Compound Nos. 5 and 6, respectively, in place of Compound No. 4 in the procedure of Example 5.

(Compound No. 8)

1-Ethyl-6,7-dihydropyrrolo[2,3-c]azepine-4,8(1H,5H)-dione (Compound No. 9)

1-Benzyl-6,7-dihydropyrrolo[2,3-c]azepine-4,8(1H,5H)-dione

EXAMPLE 7

Synthesis of 7-(3-chloropropyl)-1-methyl-6,7-dihydropyrrolo[2,3-c]azepine-4,8(1H,5H)-dione (Compound No. 10)

In 110 ml of DMF, 0.80 g (20 mmol) of 60% sodium hydride was suspended. A solution of 3.56 g (20 mmol) of Compound No. 7 obtained in Example 5 in 10 ml of DMF was added to the above suspension under a nitrogen stream, ice cooling and stirring, followed by stirring at 60° C. for 10 minutes. The reaction mixture was thereafter ice-cooled, to which 9.04 g (80 mmol) of 1,3-dichloropropane were added under stirring. The resulting mixture was stirred at 0° C. for one hour and then at room temperature for 30 minutes. The reaction mixture was concentrated under reduced pressure. The oil so obtained was added with 500 ml of a 3:1 v/v mixed solvent of ethyl acetate and benzene. The organic layer was washed successively with a 10% aqueous solution of citric acid, water and saturated saline, followed by drying over anhydrous sodium sulfate. The solvent was then distilled off under reduced pressure. The resultant oil was purified by chromatography on a silica gel column in which silica gel "Art. 9385" (product of Merck & Co.; the same silica gel was also used in the subsequent examples) was used as silica gel (eluent: 1:1 mixed solvent of ethyl acetate and hexane), whereby 1.84 g of the title compound were obtained (yield: 36%).

Although this compound was sufficiently pure, it can be recrystallized from isopropyl ether as needed.

EXAMPLE 8

Compound Nos. 11 and 12 were obtained using 1,4-dibromobutane and 1,5-dichloropentane, respectively, in place of 1,3-dichloropropane in the procedure of Example 7.

(Compound No. 11)

7-(4-bromobutyl)-1-methyl-6,7-dihydropyrrolo[2,3-c]azepine-4,8(1H,5H)-dione (Compound No. 12)

7-(5-chloropenthyl)-1-methyl-6,7-dihydropyrrolo[2,3-c]azepine-4,8(1H,5H)-dione

EXAMPLE 9

Compound Nos. 13 and 14 were obtained using Compound Nos. 8 and 9, respectively, in place of Compound No. 7 in the procedure of Example 7.

(Compound No. 13)

7-(3-Chloropropyl)-1-ethyl-6,7-dihydropyrrolo[2,3-c]azepine-4,8(1H,5H)-dione (Compound No. 14)

1-Benzyl-7-(3-chloropropyl)-6,7-dihydropyrrolo[2,3-c]azepine-4,8(1H,5H)-dione

EXAMPLE 10

Synthesis of 7-(3-chloropropyl)-4-hydroxyimino-1-methyl-4,5,6,7-tetrahydropyrrolo[2,3-c]azepin-8(1H)-one (Compound No. 15)

A solution of 371 mg (1.45 mmol) of Compound No. 10 obtained in Example 7 and 121 mg (1.74 mmol) of hydroxylamine hydrochloride in 25 ml of pyridine was stirred at 70° C. for 8 hours. The reaction mixture was concentrated under reduced pressure. The residue was added with chloroform and washed successively with a half-saturated aqueous solution of potassium carbonate, water and saturated saline, followed by drying over anhydrous sodium sulfate. The solvent was distilled off under reduced pressure and the resulting oil was purified by chromatography on a silica gel column (eluent: 1:1 mixed solvent of ethyl acetate and hexane), whereby 190 mg of the title compound were obtained (yield 49%).

EXAMPLE 11

Compound No. 16 was obtained using Compound No. 13 in place of Compound No. 10 in the procedure of Example 10.

(Compound No. 16)

7-(3-Chloropropyl)-1-ethyl-4-hydroxyimino-4,5,6,7-tetrahydropyrrolo[2,3-c]azepin-8(1H)-one

EXAMPLE 12

Synthesis of 1-methyl-7-[4-(4-phenylpiperazin-1-yl)butyl]-6,7-dihydropyrrolo[2,3-c]azepine-4,8(1H,5H)-dione (Compound No. 17)

A suspension of 157 mg (0.5 mmol) of Compound No. 11 obtained in Example 8, 243 mg (1.5 mmol) of 1-phenylpiperazine and 75 mg (0.5 mmol) of sodium iodide in 15 ml of DMF was stirred at room temperature for 3 hours. The solvent was thereafter distilled off under reduced pressure. The residue was added with a 3:1 v/v mixed solvent of ethyl acetate and benzene and water. The resulting mixture was allowed to separate into layers. The organic layer was successively washed with a saturated aqueous solution of sodium hydrogencarbonate and saturated saline, followed by drying over anhydrous sodium sulfate.

The solvent was distilled off under reduced pressure and the resulting oil was purified by chromatography on a silica gel column (eluent: 3% methanol in chloroform), whereby 190 mg of the title compound were obtained (yield: 96%).

Although this compound was sufficiently pure, it can be recrystallized from ethyl acetate-ethyl ether as needed.

EXAMPLE 13

Compound Nos. 18, 19 and 20 were obtained by conducting the reaction using Compound Nos. 10, 13 and 14, respectively at temperatures of 80°–100° C., in place of Compound No. 11 in the procedure of Example 12.

(Compound No. 18)

1-Methyl-7-[3-(4-phenylpiperazin-1-yl)propyl]-6,7-dihydropyrrolo[2,3-c]azepine-4,8(1H,5H)-dione (Compound No. 19)

1-Ethyl-7-[3-(4-phenylpiperazin-1-yl)propyl]-6,7-dihydropyrrolo[2,3-c]azepine-4,8(1H,5H)-dione (Compound No. 20)

1-Benzyl-7-[3-(4-phenylpiperazin-1-yl)propyl]-6,7-dihydropyrrolo[2,3-c]azepine-4,8(1H,5H)-dione

EXAMPLE 14

Compound No. 21 was obtained using 4-phenylpiperidine in place of 1-phenylpiperazine in the procedure of Example 12.

(Compound No. 21)

1-Methyl-7-[4-(4-phenylpiperidin-1-yl)butyl]-6,7-dihydropyrrolo[2,3-c]azepine-4,8(1H,5H)-dione

EXAMPLE 15

Compound No. 22 was obtained by conducting the reaction using Compound No. 10 and 1-(3-methoxyphenyl)piperazine at the temperature of 80° C. in place of Compound No. 11 and 1-phenylpiperazine in the procedure of Example 12.

(Compound No. 22)

7-[3-[4-(3-methoxyphenyl)piperazin-1-yl]propyl]-1-methyl-6,7-dihydropyrrolo[2,3-c]azepine-4,8(1H,5H)-dione

EXAMPLE 16

Synthesis of 7-[3-[4-(4-methoxyphenyl)piperazin-1-yl]propyl]-1-methyl-6,7-dihydropyrrolo[2,3-c]azepine-4,8(1H,5H)-dione (Compound No. 23)

A suspension of 200 mg (0.79 mmol) of Compound No. 10 obtained in Example 7, 623 mg (2.36 mmol) of 1-(4-methoxyphenyl)piperazine dihydrochloride, 652 mg (4.72 mmol) of potassium carbonate and 118 mg (0.79 mmol) of sodium iodide in 20 ml of DMF was stirred at 80° C. for 6 hours. The reaction mixture was then treated as in Example 12, whereby 155 mg of the title compound were obtained (yield: 48%).

EXAMPLE 17

Compound Nos. 24, 25, 26 and 27 were obtained using 1-(2-pyrimidinyl)piperazine dihydrochloride, 4-(4-fluorophenoxy)piperidine hydrochloride, 4-(4-fluorophenylthio)piperidine hydrochloride and 2-phenoxyethylamine, respectively, in place of 1-(4-methoxyphenyl)piperazine dihydrochloride in the procedure of Example 16.

(Compound No. 24)

1-Methyl-7-[3-[4-(2-pyrimidinyl)piperazin-1-yl]propyl]-6,7-dihydropyrrolo[2,3-c]azepine-4,8(1H,5H)-dione (Compound No. 25)

7-[3-[4-(4-fluorophenoxy)piperidin-1-yl]propyl]-1-methyl-6,7-dihydropyrrolo[2,3-c]azepine-4,8(1H,5H)-dione (Compound No. 26)

7-[3-[4-(4-fluorophenylthio)piperidin-1-yl]-propyl]-1-methyl-6,7-dihydropyrrolo[2,3-c]azepine-4,8(1H,5H)-dione (Compound No. 27)

1-Methyl-7-[3-(2-phenoxyethylamino)propyl]-6,7-dihydropyrrolo[2,3-c]azepine-4,8(1H,5H)-dione

EXAMPLE 18

Compound Nos. 28 and 29 were obtained by conducting reactions in a similar manner to Example 16 except that triethylamine was used in place of potassium carbonate and in addition, N-methyl-3,4-dimethoxyphenethylamine hydrochloride and 4-(4-fluorobenzoyl)piperidine hydrochloride were used respectively in place of 1-(4-methoxyphenyl)piperazine dihydrochloride.

(Compound No. 28)

1-Methyl-7-[3-[N-methyl-N-[2-(3,4-dimethoxyphenyl)ethyl]amino]propyl]-6,7-dihydropyrrolo[2,3-c]azepine-4,8(1H,5H)-dione (Compound No. 29)

7-[3-[4-(4-fluorobenzoyl)piperidin-1-yl]propyl]-1-methyl-6,7-dihydropyrrolo[2,3-c]azepine-4,8(1H,5H)-dione

EXAMPLE 19

Compound No. 30 was obtained by conducting reaction in a similar manner to Example 16 except that Compound No. 13 and 4-(4-fluorobenzoyl)piperidine hydrochloride were used in place of Compound No. 10 and 1-(4-methoxyphenyl)piperazine dihydrochloride.

(Compound No. 30)

1-Ethyl-7-[3-[4-(4-fluorobenzoyl)piperidin-1-yl]propyl]-6,7-dihydropyrrolo[2,3-c]azepine-4,8(1H,5H)-dione

EXAMPLE 20

Synthesis of 7-[3-[4-(4-fluorophenyl)piperazin-1 -yl]-propyl]-1-methyl-6,7-dihydropyrrolo[2,3-c]azepine-4,8(1H,5H)-dione (Compound No. 31)

To a suspension of 480 mg (12 mmol) of 60% sodium hydride in 60 ml of DMF, a solution of 1.78 g (10 mmol) of Compound 7 obtained in Example 5 in 20 ml of DMF was gradually added under cooling and stirring. The reaction mixture was stirred at room temperature for one hour and then at 40° C. for 10 minutes, followed by the addition of a solution of 3.85 g (15 mmol) of 1-(3-chloropropyl)-4-(4-fluorophenyl)piperazine in 20 ml of DMF at room temperature. The resulting solution was stirred at room temperature for 16 hours.

The reaction mixture was added with a 2:1 v/v mixed solvent of ethyl acetate and benzene and the organic layer was washed successively with a half-saturated aqueous solution of potassium carbonate, water (thrice) and saturated saline, followed by drying over anhydrous sodium sulfate. The solvent was distilled off under reduced pressure and the resultant oil was purified by chromatography on a silica gel column (eluent: ethyl acetate→5% methanol in chloroform), whereby 1.71 g of the title compound were obtained (yield: 43%).

EXAMPLE 21

Compound No. 32 was obtained by conducting a reaction in a similar manner to Example 20 except that Compound No. 8 was used in place of Compound No. 7.

(Compound No. 32)

1-Ethyl-7-[3-[4-(4-fluorophenyl)piperazin-1-yl]propyl]-6,7-dihydropyrrolo[2,3-c]azepine-4,8(1H,5H)-dione

EXAMPLE 22

Synthesis of 7-[5-(1-imidazolyl)pentyl]-1-methyl-6,7-dihydropyrrolo[2,3-c]azepine-4,8(1H,5H)-dione (Compound No. 33)

A suspension of 68 mg (1 mmol) of imidazole and 40 mg (1 mmol) of 60% sodium hydride in 15 ml of DMF was stirred at room temperature for one hour under a nitrogen stream, followed by the gradual addition of a solution of 283 mg (1 mmol) of Compound No. 12 obtained in Example 8 in 5 ml of DMF. The resulting solution was stirred at 80° C. for 16 hours. The reaction mixture was concentrated under reduced pressure and the residue was purified by chromatography on a silica gel column (eluent: ethyl acetate→10% methanol in chloroform), whereby 84 mg of the title compound were obtained (yield: 27%).

EXAMPLE 23

Synthesis of 1-methyl-8-[3-(4-phenylpiperidin-1-yl)propoxy]-5,6-dihydropyrrolo[2,3-c]azepin-4(1H)-one (Compound No. 34)

A suspension of 300 mg (1.18 mmol) of Compound No. 10 obtained in Example 7, 570 mg (3.53 mmol) of 4-phenylpiperidine and 488 mg (3.53 mmol) of potassium carbonate in 30 ml of DMF was stirred at 80° C. for 15 hours. The reaction mixture was added with 400 ml of a 3:1 v/v mixed solvent of ethyl acetate and benzene and washed successively with water and saturated saline, followed by drying over anhydrous sodium sulfate. The solvent was distilled off under reduced pressure and the residue was purified by chromatography on a silica gel column (eluent: 2:1 mixed solvent of ethyl acetate and hexane), whereby 270 mg of the title compound were obtained (yield: 60%) from a first fraction.

In addition, Compound No. 35 was obtained from the next fraction.

(Compound No. 35)

1-Methyl-7-[3-(4-phenylpiperidin-1-yl)propyl]-6,7-dihydropyrrolo[2,3-c]azepine-4,8(1H,5H)-dione

EXAMPLE 24

Compound Nos. 36 and 37 and Compound Nos. 38 and 18 were obtained successively using 1-(2-methoxyphenyl)piperazine and 1-phenylpiperazine, respectively, in place of 4-phenylpiperidine in the procedure of Example 23.

(Compound No. 36)

8-[3-[4-(2-Methoxyphenyl)piperazin-1-yl]propoxy]-1-methyl-5,6-dihydropyrrolo[2,3-c]azepin-4(1H)-one (Compound No. 37)

7-[3-[4-(2-Methoxyphenyl)piperazin-1-yl]propyl]-1-methyl-6,7-dihydropyrrolo[2,3-c]azepine-4,8(1H,5H)-dione (Compound No. 38)

1-Methyl-8-[3-(4-phenylpiperazin-1-yl)propoxy]-5,6-dihydropyrrolo[2,3-c]azepin-4(1H)-one (Compound No. 18)

1-Methyl-7-[3-(4-phenylpiperazin-1-yl)propyl]-6,7-dihydropyrrolo[2,3-c]azepine-4,8(1H,5H)-dione

EXAMPLE 25

Synthesis of 4-hydroxy-1-methyl-7-[3-(4-phenylpiperazin-1-yl)propyl]-4,5,6,7-tetrahydropyrrolo[2,3-c]azepin-8(1H)-one (Compound No. 39)

In 15 ml of methanol, 158 mg (0.41 mmol) of Compound No. 18 obtained in Example 13 were dissolved. The resulting solution was gradually added with 31 mg (0.83 mmol) of sodium borohydride under cooling and stirring, followed by stirring at 0° C. for 30 minutes and then at room temperature for 2 hours. The solvent was distilled off under reduced pressure. The residue was added with saturated saline and then extracted with chloroform three times. The organic layer was dried over anhydrous sodium sulfate, followed by concentration under reduced pressure. The resultant crude product was purified by chromatography on a silica gel column (eluent: 5% methanol in chloroform), whereby 140 mg of the title compound were obtained (yield: 89%).

Although this compound was sufficiently pure, it can be recrystallized from ethyl acetate as needed.

EXAMPLE 26

Compound Nos. 40 and 41 were obtained by conducting reactions in a similar manner to Example 25 except that Compound Nos. 31 and 36 were used, respectively, in place of Compound No. 18.

(Compound No. 40)

7-[3-[4-(4-Fluorophenyl)piperazin-1-yl]propyl]-4-hydroxy-1-methyl-4,5,6,7-tetrahydropyrrolo[2,3-c]azepin-8(1H)-one (Compound No. 41)

4-Hydroxy-1-methyl-8-[3-[4-(2-methoxyphenyl)piperazine-1-yl]propoxy]-1,4,5,6-tetrahydropyrrolo[2,3-c]azepine

EXAMPLE 27

Synthesis of 1-methyl-7-[3-(4-phenylpiperazin-1-yl)Propyl]-6,7-dihydropyrrolo[2,3-c]azepin-8(1H)-one (Compound No. 42)

In 10 ml of chloroform, 100 mg (0.26 mmol) of Compound No. 39 obtained in Example 25 were dissolved. The resulting solution was added with 6 ml of a chloroform solution which was saturated with HCl, followed by stirring at room temperature for one hour. The reaction mixture was concentrated under reduced pressure and then added with a saturated aqueous solution of potassium carbonate and chloroform. The resulting mixture was allowed to separate into layers. The organic layer was washed with saturated saline, followed by drying over anhydrous sodium sulfate. The solvent was distilled off under reduced pressure and the resulting oil was purified by chromatography on a silica gel column (eluent: 5% methanol in chloroform), whereby 50 mg of the title compound were obtained (yield: 53%).

EXAMPLE 28

Compound Nos. 43 and 44 were obtained using Compound No. 15 and 4-(4-fluorobenzoyl)piperidine hydrochloride in combination and Compound No. 16 and 4-(4-fluorobenzoyl)piperidine p-toluenesulfonate in combination, respectively, in place of the combination of Compound No. 10 and 1-(4-methoxyphenyl)piperazine dihydrochloride in the procedure of Example 16.

(Compound No. 43)

7-[3-[4-(4-Fluorobenzoyl)piperidin-1-yl]propyl]-4-hydroxyimino-1-methyl-4,5,6,7-tetrahydropyrrolo[2,3-c]azepin-8H)-one (Compound No. 44)

1-Ethyl-7-[3-[4-(4-fluorobenzoyl)piperidin-1-yl]Propyl]-4-hydroxyimino-4,5,6,7-tetrahydropyrrolo[2,3-c]azepin-8(1H)-one

EXAMPLE 29

Synthesis of 4-hydroxyimino-1-methyl-7-[3-(4-phenylpiperazin-1-yl)propyl]-4,5,6,7-tetrahydropyrrolo[2,3-c]azepin-8(1H)-one (Compound No. 45)

A solution of 1073 g (2.82 mmol) of compound No. 18 obtained in Example 13 and 0.275 g (3.38 mmol) of hydroxylamine hydrochloride in 50 ml of pyridine was stirred at 70° C. for 14 hours. The solvent was distilled off under reduced pressure. The residue was added with a half-saturated aqueous solution of potassium carbonate and extracted with chloroform three times. The chloroform layer was washed with saturated saline, followed by drying over anhydrous sodium sulfate. The solvent was distilled off under reduced pressure and the residue was purified by chromatography on a silica gel column (eluent: ethyl acetate), whereby 1.074 g of the title compound were obtained (yield: 96%).

Although this compound was sufficiently pure, it can be recrystallized from methanol-isopropyl ether as needed.

EXAMPLE 30

Compound No. 46 was obtained using O-methylhydroxylamine hydrochloride in place of hydroxylamine hydrochloride in the procedure of Example 29.

(Compound No. 46)

4-Methoxyimino-1-methyl-7-[3-(4-phenylpiperazin-1-yl)propyl]-4,5,6,7-tetrahydropyrrolo[2,3-c]azepin-8(1H)-one

EXAMPLE 31

Compound Nos. 47, 48, 49, 50, 51, 52, 53 and 54 were obtained using Compound Nos. 19, 20, 37, 22, 23, 35, 21 and 17, respectively, in place of Compound No. 18 in the procedure of Example 29.

(Compound No. 47)

1-Ethyl-4-hydroxyimino-7-[3-(4-phenylpiperazin-1-yl)propyl]-4,5,6,7-tetrahydropyrrolo[2,3-c]azepin-8(1H)-one (Compound No. 48)

1-Benzyl-4-hydroxyimino-7-[3-(4-phenylpiperazin-1-yl)propyl]-4,5,6,7-tetrahydropyrrolo[2,3-c]azepin-8(1H)-one (Compound No. 49)

4-Hydroxyimino-7-[3-[4-(2-methoxyphenyl)piperazin-1-yl]propyl]-1-methyl-4,5,6,7-tetrahydropyrrolo[2,3-c]azepin-8(1H)-one (Compound No. 50)

4-Hydroxyimino-7-[3-[4-(3-methoxyphenyl)piperazin-1-yl]propyl]-1-methyl-4,5,6,7-tetrahydropyrrolo[2,3-c]azepin-8(1H)-one (Compound No. 51)

4-Hydroxyimino-7-[3-[4-(4-methoxyphenyl)piperazin-1-yl]propyl]-1-methyl-4,5,6,7-tetrahydropyrrolo[2,3-c]azepin-8(1H)-one (Compound No. 52)

4-Hydroxyimino-1-methyl-7-[3-(4-phenylpiperidin-1-yl)propyl]-4,5,6,7-tetrahydropyrrolo[2,3-c]azepin-8(1H)-one (Compound No. 53)

4-Hydroxyimino-1-methyl-7-[4-(4-phenylpiperidin-1-yl)butyl]-4,5,6,7-tetrahydropyrrolo[2,3-c]azepin-8(1H)-one (Compound No. 54)

4-Hydroxyimino-1-methyl-7-[4-(4-phenylpiperazin-1-yl)butyl]-4,5,6,7-tetrahydropyrrolo[2,3-c]azepin-8(1H)-one

EXAMPLE 32

Synthesis of 4-hydroxyimino-1-methyl-7-[3-[4-(2-pyrimidinyl)piperazin-1-yl]propyl]-4,5,6,7-tetrahydropyrrolo[2,3-c]azepin-8(1H)-one (Compound No. 55)

A suspension of 180 mg (0.47 mmol) of Compound No. 24 obtained in Example 17, 65 mg (0.94 mmol) of hydroxylamine hydrochloride and 77 mg (0.94 mmol) of sodium acetate in 30 ml of methanol was refluxed for 19 hours. The reaction mixture was concentrated under reduced pressure. The residue was added with a half-saturated aqueous solution of potassium carbonate and then extracted with chloroform (three times). The organic layer was washed successively with water and saturated saline, followed by drying over anhydrous sodium sulfate. The solvent was thereafter distilled off under reduced pressure. The resultant oil was purified by chromatography on a silica gel column (eluent: 5% methanol in chloroform), whereby 179 mg of the title compound were obtained (yield: 96%).

EXAMPLE 33

Compound Nos. 56, 57, 58 and 59 were obtained using Compound Nos. 31, 32, 25 and 26, respectively, in place of Compound No. 24 in the procedure of Example 32.

(Compound No. 56)

7-[3-[4-(4-Fluorophenyl)piperazin-1-yl]propyl]-4-hydroxyimino-1-methyl-4,5,6,7-tetrahydropyrrolo[2,3-c]azepin-8(1H)-one (Compound No. 57)

1-Ethyl-7-[3-[4-(4-fluorophenyl)piperazin-1-yl]propyl]-4-hydroxyimino-4,5,6,7-tetrahydropyrrolo[2,3-c]azepin-8(1H)-one (Compound No. 58)

7-[3-[4-(4-Fluorophenoxy)piperidin-1-yl]propyl]-4-hydroxyimino-1-methyl-4,5,6,7-tetrahydropyrrolo[2,3-c]azepin-8(1H)-one (compound No. 59)

7-[3-[4-(4-Fluorophenylthio)piperidin-1 yl]propyl]-4-hydroxyimino-1-methyl-4,5,6,7-tetrahydropyrrolo[2,3-c]azepin-8(1H)-one

EXAMPLE 34

Compound Nos. 60, 61 and 62 were obtained using Compound Nos. 34, 36 and 38, respectively, in place of Compound No. 18 in the procedure of Example 29.

(Compound No. 60)

1-Methyl-8-[3 -(4-phenylpiperidin-1-yl)propoxy]-5,6-dihydropyrrolo [2,3-c]azepin-4 (1H) -one oxime (Compound No. 61)

8-[3-[4-(2-Methoxyphenyl)piperazin-1-yl]propoxy]-1-methyl-5,6-dihydropyrrolo[2,3-c]azepin-4(1H)-one oxime (Compound No. 62)

1-Methyl-8-[3-(4-phenylpiperazin-1-yl)propoxy]-5,6-dihydropyrrolo[2,3-c]azepin-4(1H)-one oxime Data of the physical properties of the compounds obtained in the above examples are summarized in Table 1.

TABLE 1

| Comp'd No. | Property Melting point (recrystallization solvent) | NMR*1 (δ ppm/270 MHz) | IR*2 (cm⁻¹) | Yield (%) | Structural formula |
|---|---|---|---|---|---|
| 7 | Colorless prism crystals 196.0–198.0° C. (acetonitrile) | 2.82(2H,m), 3.52(2H,m), 3.97(3H,s), 6.72(1H,d,J = 2.6 Hz), 6.79(1H,d,J = 2.6 Hz), 6.96(1H,br.) | 3410, 1645, 1485, 1460, 1355, 1315, 1100 | 67 | (structure: bicyclic ketone-lactam with N—CH$_3$) |
| 8 | Colorless prism crystals 157.0–158.5° C. (ethyl acetate) | 1.45(3H,t,J = 7.3 Hz), 2.83(2H,m), 3.53(2H,m), 4.41(2H,q,J = 7.3 Hz), 6.35(1H,br.), 6.74(1H,d,J = 2.6 Hz), 6.86(1H,d,J = 2.6 Hz) | 3420, 1655, 1485, 1465, 1375, 1320, 1120, 895 | 73 | (structure: bicyclic ketone-lactam with N—C$_2$H$_5$) |
| 9 | Colorless needle crystals 148.0–149.0° C. (ethyl acetate-hexane) | 2.80(2H,m), 3.46(2H,m), 5.63(2H,s), 6.76(1H,d,J = 2.6 Hz), 6.85(1H,d,J = 2.6 Hz), 7.05(1H, br.t), 7.13(2H,dd,J = 7.3 Hz, 2.1 Hz), 7.21–7.39(3H,m) | 3420, 1655, 1485, 1470, 1375, 1320, 1115, 895 | 60 | (structure: bicyclic ketone-lactam with N—CH$_2$Ph) |
| 10 | Colorless prism crystals 80.0–81.0° C. (isopropyl ether) | 2.15(2H,m), 2.79(2H,m), 3.63(2H,t,J = 6.3 Hz), 3.66–3.85(4H,m), 3.93(3H,s), 6.64(1H,d, J = 3.0 Hz), 6.75(1H,d,J = 3.0 Hz) | 2940, 1655, 1630, 1485, 1425, 1375, 1290, 1105 | 36 | (structure: bicyclic ketone with N—(CH$_2$)$_3$Cl side chain and N—CH$_3$) |

TABLE 1-continued

| Comp'd No. | Property Melting point (recrystallization solvent) | NMR*1 (δ ppm/270 MHz) | IR*2 (cm⁻¹) | Yield (%) | Structural formula |
|---|---|---|---|---|---|
| 11 | Colorless plate crystals 77.0–78.0° C. (isopropyl ether) | 1.82(2H,m), 1.92(2H,m), 2.80 (2H,m), 3.48(2H,t,J = 6.3 Hz), 3.56–3.77(4H,m), 3.93(3H,s), 6.64(1H,d,J = 3.3 Hz), 6.74(1H,d,J = 3.3 Hz) | 2950, 1640, 1480, 1430, 1380, 1315, 1220, 1045 | 53 | N–(CH₂)₄Br ring with N–CH₃ |
| 12 | Colorless oil | 1.53(2H,m), 1.68(2H,m), 1.83(2H,m), 2.78(2H,m), 3.48–3.63(4H,m), 3.68 (2H,m), 3.93(3H,s), 6.63 (1H,d,J = 2.6 Hz), 6.74 (1H,d,J = 2.6 Hz) | 2930, 1655, 1630, 1485, 1475, 1425, 1375, 1305, 1105 | 43 | N–(CH₂)₅Cl ring with N–CH₃ |
| 13 | Colorless oil | 1.26(3H,t,J = 7.3 Hz), 2.14 (2H,m), 2.79(2H,m), 3.63 (2H,t,J = 6.3 Hz), 3.66–3.83 (4H,m), 4.35(2H,q,J = 7.3 Hz), 6.66(1H,d,J = 3.0 Hz), 6.83(1H,d,J = 3.0 Hz) | 2950, 1640, 1480, 1435, 1380, 1285, 1050 | 72 | N–(CH₂)₃Cl ring with N–C₂H₅ |
| 14 | Colorless powdery crystals | 1.99(2H,m), 2.79(2H,dd, J = 5.9 Hz, 4.0 Hz), 3.40(2H,t, J = 6.6 Hz), 3.52–3.80(4H,m), 5.56(2H,s), 6.67(1H,d,J = 2.6 Hz), 6.86(1H,d,J = 2.6 Hz), 7.12(2H,m), 7.20–7.45(3H,m) | (KBr) 1663, 1634, 1482, 1454, 1431, 1378, 1309, 1250, 1186, 1136, 927 | 46 | N–(CH₂)₃Cl ring with N–CH₂Ph |

TABLE 1-continued

| Comp'd No. | Property Melting point (recrystallization solvent) | NMR*1 (δ ppm/270 MHz) | IR*2 (cm⁻¹) | Yield (%) | Structural formula |
|---|---|---|---|---|---|
| 15 | Colorless powdery crystals | 2.12(2H,m), 3.01(2H,m), 3.50–3.73(6H,m), 3.88 (3H,s), 6.46(1H,d,J = 2.7 Hz), 6.71(1H,d,J = 2.7 Hz), 7.70(1H,br.s) | 1625, 1485, 1420, 1375, 1100 | 49 | (structure: NOH, N-(CH₂)₃Cl, N-CH₃) |
| 16 | Colorless needle crystals 142.0–145.0° C. (ethanol) | 1.40(3H,t,J = 7.3 Hz), 2.13(2H,m), 2.97(2H,m), 3.48–3.77(6H,m), 4.29(2H,q,J = 7.3 Hz), 6.39(1H,d,J = 2.6 Hz), 6.79(1H,d,J = 2.6 Hz), 7.41(1H,br.s) | (KBr) 2980, 1626, 1476, 1437, 1376, 1303, 1244, 1019, 914 | 41 | (structure: NOH, N-(CH₂)₃Cl, N-C₂H₅) |
| 17 | Colorless prism crystals 126.0–127.0° C. (ethyl acetate-ethyl ether) | 1.55–1.80(4H,m), 2.49 (2H,t,J = 7.2 Hz), 2.60–2.70(4H,m), 2.79(2H,t, J = 5.3 Hz), 3.15–3.30 (4H,m), 3.62(2H,t,J = 7.2 Hz), 3.66(2H,m), 3.93(3H,s), 6.64(1H,d, J = 2.6 Hz), 6.74(1H,d,J = 2.6 Hz), 6.86(1H,t,J = 7.2 Hz), 6.93(2H,d,J = 7.2 Hz), 7.26(2H,t,J = 7.2 Hz) | 2950, 2820, 1660, 1630, 1600, 1490, 1480, 1380, 1300, 990, 905 | 96 | (structure: O, N-(CH₂)₄N-piperazine-phenyl, N-CH₃) |
| 18 | Yellow oil | 1.90(2H,m), 2.45(2H,t,J = 7.3 Hz), 2.54–2.70(4H,m), 2.79(2H,m), 3.10–3.30(4H,m), 3.58–3.78(4H,m), 3.92(3H,s), 6.63(1H,d,J = 3.3 Hz), 6.73 (1H,d,J = 3.3 Hz), 6.84(1H, t,J = 7.3 Hz), 6.92(2H,d, J = 7.3 Hz), 7.25(2H,d,J = 7.3 Hz) | 2940, 2820, 1660, 1630, 1595, 1490, 1380, 1145, 910 | 97 | (structure: O, N-(CH₂)₃N-piperazine-phenyl, N-CH₃) |

TABLE 1-continued

| Comp'd No. | Property Melting point (recrystallization solvent) | NMR*1 (δ ppm/270 MHz) | IR*2 (cm⁻¹) | Yield (%) | Structural formula |
|---|---|---|---|---|---|
| 19 | Colorless oil | 1.44(3H,t,J = 7.2 Hz), 1.91 (2H,m), 2.50(2H,t,J = 7.2 Hz), 2.55–2.70(4H,m), 2.78(2H,t,J = 3.15–3.30(4H,m), 3.65(2H,t, J = 7.2 Hz), 3.69(2H,m), 4.35(2H, q,J = 7.2 Hz), 6.65(1H,d,J = 3.0 Hz), 6.82(1H,d,J = 3.0 Hz), 6.86(1H,t, J = 7.3 Hz), 6.93(2H,d,J = 7.3 Hz), 7.27(2H,t,J = 7.3 Hz) | 2950, 2830, 1665, 1640, 1600, 1490, 1380, 1150, 995 | 88 | |
| 20 | Colorless oil | 1.79(2H,m), 2.36(2H,t,J = 7.3 Hz), 2.56(4H,m), 2.79(2H,m), 3.19(4H,m), 3.50–3.77(4H,m), 5.58(2H,s), 6.67(1H,d,J = 2.7 Hz), 6.79–6.90(2H,m), 6.92(2H,d,J = 7.9 Hz), 7.13(2H,d,J = 7.9 Hz), 7.20–7.39(5H,m) | 2935, 2810, 1655, 1630, 1600, 1485, 1375, 1140 | quant | |
| 21 | Yellow oil | 1.55–1.80(4H,m), 1.80–1.98 (4H,m), 2.12(2H,m), 2.40–2.60(3H,m), 2.79(2H,t,J = 5.3 Hz), 3.10(2H,m), 3.62(2H,t,J = 7.2 Hz), 3.67(2H,m), 3.93(3H,s), 6.63 (1H,d,J = 2.6 Hz), 6.74(1H,d,J = 2.6 Hz), 7.10–7.40(5H,m) | 2950, 2820, 2780, 1660, 1635, 1490, 1380, 1440, 1380, 1310, 1150, 1120, 910 | 96 | |
| 22 | Colorless oil | 1.90(2H,m), 2.49(2H,t,J = 7.3 Hz), 2.55–2.70(4H,m), 2.79(2H,m), 3.15–3.25(4H,m), 3.65(2H,t,J = 7.3 Hz), 3.70(2H,m), 3.79(3H,s), 3.39(3H,s), 6.42(1H,dd,J = 7.9 Hz, 1.9 Hz), 6.46(1H,t,J = 1.9 Hz), 6.53 (1H,dd,J = 7.9 Hz,1.9 Hz), 6.64(1H,d, J = 2.7 Hz), 6.74(1H,d,J = 2.7 Hz), 7.17(1H,t,J = 7.9 Hz) | 2950, 2830, 1660, 1635, 1490, 1380, 1165, 995 | 84 | |

TABLE 1-continued

| Comp'd No. | Property Melting point (recrystallization solvent) | NMR*1 (δ ppm/270 MHz) | IR*2 (cm⁻¹) | Yield (%) | Structural formula |
|---|---|---|---|---|---|
| 23 | Colorless powdery crystals | 1.98(2H,m), 2.59(2H,m), 2.65–2.80(m), 2.79(m), (6H in total), 3.10–3.25(4H,m), 3.66(2H,t, J = 7.3 Hz), 3.70(2H,m), 3.77 (3H,s), 3.93(3H,s), 6.64(1H,d, J = 2.6 Hz), 6.74(1H,d,J = 2.6 Hz), 6.84(2H,d,J = 9.2 Hz), 6.90(2H,d,J = 9.2 Hz) | 2820, 1660, 1630, 1600, 1490, 1370, 1140 | 48 | |
| 24 | Yellow oil | 1.90(2H,m), 2.42–2.57(6H,m), 2.80(2H,m), 3.66(2H,t,J = 7.3 Hz), 3.71(2H,m), 3.83 (4H,m), 3.93(3H,s), 6.48 (1H,t,J = 4.6 Hz), 6.63(1H,d, J = 3.0 Hz), 6.75(1H,d,J = 3.0 Hz), 8.30(2H,d,J = 4.6 Hz) | (film) 1658, 1629, 1585, 1546, 1491, 1444, 1359, 1308, 1256, 983, 780 | 55 | |
| 25 | Yellow oil | 1.69–2.05(6H,m), 2.28(2H,m), 2.43(2H,t,J = 7.3 Hz), 2.65–2.84(4H,m), 3.62(2H,t, J = 7.3 Hz),3.70(2H,m), 3.92 (3H,s), 4.21(1H,m), 6.61(1H,d,J = 3.3 Hz), 6.74 (1H,d,J = 3.3 Hz), 6.78–6.90 (2H,m), 6.94(2H,t,J = 8.6 Hz) | (film) 1661, 1633, 1504, 1493, 1246, 1206, 1045, 778, 764 | 66 | |
| 26 | Yellow oil | 1.53–1.98(6H,m), 2.04(2H,m), 2.38(2H,m), 2.77(2H,dd,J = 4.0 Hz,6.6 Hz), 2.86(2H,m), 2.95(1H,m), 3.60(2H,t,J = 7.3 Hz), 3.68(2H,m), 3.92(3H,s), 6.63(1H,d,J = 3.3 Hz), 6.73 (1H,d,J = 3.3 Hz), 6.99(2H,t, J = 8.6 Hz), 7.41(2H,m) | (film) 2943, 1662, 1632, 1490, 1433, 1377, 1245, 1220, 779 | 85 | |

TABLE 1-continued

| Comp'd No. | Property Melting point (recrystallization solvent) | NMR*1 (δ ppm/270 MHz) | IR*2 (cm⁻¹) | Yield (%) | Structural formula |
|---|---|---|---|---|---|
| 27 | Pale yellow oil | 1.89(2H,m), 2.27(1H,br.s), 2.72–2.82(4H,m), 3.03(2H, t,J = 5.3 Hz), 3.62–3.72 (4H,m), 3.90(3H,s), 4.09(2H,t,J = 5.3 Hz), 6.63 (1H,d,J = 2.6 Hz), 6.72(1H,d, J = 2.6 Hz), 6.86–6.99 (3H,m), 7.22–7.32(2H,m) | (film) 1628, 1491, 1245, 758 | 10 | ![structure with N-(CH₂)₃NHCH₂CH₂OPh] |
| 28 | Brown oil | 1.82(2H,m), 2.31(3H,s), 2.47(2H,t,J = 7.3 Hz), 2.60 (2H,m), 2.66–2.82(4H,m), 3.58(2H,t,J = 7.3 Hz), 3.63 (2H,m), 3.85(3H,s), 3.87(3H,s), 3.92(3H,s), 6.63(1H,d,J = 2.7 Hz), 6.67–6.85(4H,m) | 2940, 1660, 1635, 1595, 1375, 1230, 1140, 1025 | 51 | ![structure with 3,4-dimethoxybenzyl N-methylamine side chain] |
| 29 | Pale brown oil (hydrochloride) Colorless needle crystals 195.0–201.0° C. (methanol-isopropyl ether) | 1.75–1.99(6H,m), 2.11(2H,m), 2.44(2H,t,J = 7.3 Hz), 2.81 (2H,m), 3.03(2H,m), 3.21 (1H,m), 3.63(2H,t,J = 7.3 Hz), 3.70(2H,m), 3.93(3H,s), 6.64(1H,d,J = 3.0 Hz), 6.74(1H,d, J = 3.0 Hz), 7.14(2H,t,J = 8.6 Hz), 7.99(2H,m) | 2930, 1655, 1625, 1595, 1485, 1265, 1150, 970 | 77 | ![structure with 4-fluorobenzoyl piperidine side chain, N-CH₃] |
| 30 | Pale brown oil | 1.44(3H,t,J = 7.3 Hz), 1.50–2.50 (8H,m), 2.58(2H,m), 2.79(2H,m), 3.07(2H,m), 3.30(1H,m), 3.65 (2H,t,J = 7.3 Hz), 3.72(2H,m), 4.34(2H,q,J = 7.3 Hz), 6.65(1H,d, J = 3.0 Hz), 6.82(1H,d,J = 3.0 Hz), 7.15(2H,t,J = 8.6 Hz), 7.96(2H, dd,J = 8.6 Hz,5.3 Hz) | 2940, 1660, 1635, 1485, 1380, 1280, 1160, 975, 910 | 58 | ![structure with 4-fluorobenzoyl piperidine side chain, N-C₂H₅] |

TABLE 1-continued

| Comp'd No. | Property Melting point (recrystallization solvent) | NMR*1 (δ ppm/270 MHz) | IR*2 (cm⁻¹) | Yield (%) | Structural formula |
|---|---|---|---|---|---|
| 31 | Yellow oil (monomaleate) Pale brown prism crystals 168.0–171.0° C. (decomposed) (ethanol) | 1.87(2H,quint,J = 7.3 Hz), 2.47(2H,t,J = 7.3 Hz), 2.60(4H,m), 2.78(2H,m), 3.11(4H,m), 3.57–3.77 (4H,m), 3.92(3H,s), 6.62(1H,d,J = 3.3 Hz), 6.73(1H,d,J = 3.3 Hz), 6.80–7.00(4H,m) | (film) 1662, 1631, 1509, 1491, 1378, 1244, 1149, 816, 779 | 43 | (structure: pyrrolo-azepinone with N–CH₃, N–(CH₂)₃–piperazinyl–4-fluorophenyl) |
| 32 | Pale yellow oil | 1.44(3H,t,J = 7.3 Hz), 1.89(2H, quint,J = 7.3 Hz), 2.48(2H,t,J = 7.3 Hz), 2.62(4H,m), 2.79(2H, dd, J = 6.6 Hz,4.0 Hz), 3.13(4H,m), 3.65(2H,t,J = 7.3 Hz), 3.71(2H,m), 4.36(2H,q,J = 7.3 Hz), 6.65(1H,d, J = 2.6 Hz), 6.81(1H,d,J = 2.6 Hz), 6.83–7.01(4H,m) | (film) 2940, 2820, 1660, 1635, 1510, 1485, 1375, 1235, 1150, 925 | 25 | (structure: pyrrolo-azepinone with N–C₂H₅, N–(CH₂)₃–piperazinyl–4-fluorophenyl) |
| 33 | Pale yellow oil | 1.36(2H,m), 1.66(2H,m),1.88 (2H,m), 2.77(2H,dd,J = 6.3 Hz,4.3 Hz), 3.56(2H,t,J = 7.3 Hz), 3.65(2H,m), 3.92(s), 3.95(m), (5H in total), 6.63(1H,d,J = 3.0 Hz), 6.74(1H,d, J = 3.0 Hz), 6.91(1H,s), 7.06(1H,s), 7.50(1H,s) | (film) 2938, 1628, 1493, 1436, 1378, 1247, 1149, 1082, 918 | 27 | (structure: pyrrolo-azepinone with N–CH₃, N–(CH₂)₅–imidazol-1-yl) |
| 34 | Colorless oil | 1.55–1.90(4H,m), 2.03(2H,m), 2.66(1H,m), 2.75–2.95(4H,m), 3.60–3.80(4H,m), 3.92(3H,s), 4.20(2H,t,J = 7.2 Hz), 4.20–4.35(2H,m), 6.64(1H,d, J = 2.6 Hz), 6.74(1H,d,J = 2.6 Hz), 7.15–7.35(5H,m) | 2940, 2860, 1680, 1630, 1480, 1430, 1380, 1280, 1120, 1010, 900 | 60 | (structure: pyrrole ester with N–CH₃, O–(CH₂)₃–(4-phenylpiperidinyl)) |

TABLE 1-continued

| Comp'd No. | Property Melting point (recrystallization solvent) | NMR*1 (δ ppm/270 MHz) | IR*2 (cm$^{-1}$) | Yield (%) | Structural formula |
|---|---|---|---|---|---|
| 35 | Colorless oil | 1.75–2.00(6H,m), 2.10 (2H,m), 2.48(2H,t,J = 7.2 Hz), 2.65(1H,m), 2.80(2H,m), 3.00–3.15(2H,m), 3.65(2H, t,J = 7.2 Hz), 3.70(2H,m), 3.93(3H,s), 6.64(1H,d, J = 2.7 Hz), 6.74(1H,d,J = 2.7 Hz), 7.15–7.35(5H,m) | 2930, 2800, 1650, 1630, 1485, 1470, 1430, 1375, 1140, 1110 | 34 | (structure: pyrrole-fused ketolactam with N–(CH$_2$)$_3$N–(4-phenylpiperidine), N–CH$_3$) |
| 36 | Colorless oil | 2.03(2H,m), 2.81(2H,t, J = 5.6 Hz), 2.90–3.15(4H,m), 3.55–3.80(8H,m), 3.88(3H,s), 3.93(3H,s), 4.21(2H,t, J = 7.3 Hz), 6.64(1H,d,J = 2.7 Hz), 6.74(1H,d,J = 2.7 Hz), 6.80–7.10(4H,m) | 2950, 2830, 1690, 1640, 1490, 1430, 1380, 1150, 1120, 1020, 910 | 50 | (structure: pyrrole ester with O(CH$_2$)$_3$N–piperazine–(2-methoxyphenyl), N–CH$_3$) |
| 37 | Pale yellow oil | 1.92(2H,m), 2.53(2H,t,J = 7.2 Hz), 2.60–2.78(m), 2.80(m), (6H in total), 3.00–3.20(4H,m), 3.65(2H,t, J = 7.2 Hz), 3.70(2H,m), 3.86 (3H,s), 3.93(3H,s), 6.64(1H, d,J = 2.6 Hz), 6.74(1H,d, J = 2.6 Hz), 6.80–7.05(4H,m) | 2950, 2830, 1660, 1630, 1490, 1380, 1150, 1110, 1020, 910 | 29 | (structure: pyrrole ketolactam with N–(CH$_2$)$_3$N–piperazine–(2-methoxyphenyl), N–CH$_3$) |
| 38 | Colorless needle crystals 107.0–110.0° C. (ethyl acetate) | 2.03(2H,m), 2.80(2H,m), 3.05–3.25(4H,m), 3.55–3.80(8H,m), 3.92(3H,s), 4.21(2H,t,J = 6.6 Hz), 6.64 (1H,d,J = 2.7 Hz), 6.74(1H,d, J = 2.7 Hz), 6.85–7.00(3H,m), 7.29(2H,t,J = 7.9 Hz) | 3650, 2950, 2820, 1690, 1630, 1600, 1480, 1430, 1380, 1120, 930 | 26 | (structure: pyrrole ester with O(CH$_2$)$_3$N–piperazine–N–phenyl, N–CH$_3$) |

TABLE 1-continued

| Comp'd No. | Property Melting point (recrystallization solvent) | NMR*1 (δ ppm/270 MHz) | IR*2 (cm−1) | Yield (%) | Structural formula |
|---|---|---|---|---|---|
| 39 | Colorless prism crystals 128.0–131.0° C. (ethyl acetate) | 1.87(2H,m), 2.05–2.30(3H,m), 2.48(2H,t,J = 7.3 Hz), 2.55–2.70 (4H,m), 3.15–3.25(4H,m), 3.30– 3.65(m), 3.58(t,J = 7.3 Hz) (4H in total), 3.87(3H,s), 4.91(1H,m), 6.16(1H,d,J = 2.6 Hz), 6.71(1H,d,J = 2.6 Hz), 6.85(1H,t,J = 7.3 Hz), 6.92 (2H,d,J = 7.3 Hz), 7.26(2H,t,J = 7.3 Hz) | 3650, 3580, 3400, 2930, 2820, 1600, 1470, 1420, 1300, 970, 900 | 89 | |
| 40 | Colorless needle crystals 133.5–134.5° C. (ethyl acetate) | 1.85(2H,quint,J = 7.3 Hz), 2.03–2.31(3H,m), 2.47(2H,dt, J = 2.0 Hz, 7.3 Hz), 2.63(4H,m), 3.12(4H,m), 3.35(1H,ddd,J = 3.3 Hz, 7.3 Hz,14.9 Hz), 3.48–3.63(3H,m) 3.87(3H,s), 4.91(1H,t,J = 5.3 Hz), 6.16(1H,d,J = 2.6 Hz), 6.71(1H,d,J = 2.6 Hz), 6.82–7.03(4H,m) | (KBr) 3378, 1601, 1508, 1443, 1237, 1132, 1049, 1002, 979, 822, 776 | 67 | |
| 41 | Colorless oil | 1.99(2H,m), 2.07–2.30(3H,m), 3.00(4H,m), 3.33(1H,ddd,J = 3.3 Hz, 6.4 Hz,14.8 Hz), 3.47–3.75(7H,m), 3.86(3H,s), 3.87(3H,s), 4.20 (2H,t,J = 6.3 Hz), 4.91(1H,m), 6.16(1H,d,J = 2.6 Hz), 6.70(1H,d, J = 2.6 Hz), 6.85–7.10(4H,m) | (film) 3448, 1698, 1616, 1500, 1435, 1241, | 99 | |
| 42 | Brown oil | 1.84(2H,m), 2.44(2H,t, J = 7.3 Hz), 2.50–2.70 (4H,m), 3.15–3.30(4H,m), 3.60(2H,t,J = 7.3 Hz), 3.69(2H,t,J = 6.6 Hz), 3.96(3H,s), 5.96(1H, dt,J = 9.3 Hz,6.6 Hz), 6.09(1H,d,J = 2.6 Hz), 6.74(1H,d,J = 2.6 Hz), 6.75(1H,d,J = 9.3 Hz), 6.85(1H,t,J = 7.3 Hz), 6.92(2H,d,J = 7.3 Hz), 7.26(2H,t,J = 7.3 Hz) | 2930, 2820, 1595, 1490, 1460, 1420, 1370, 1305, 1100, 995 | 53 | |

TABLE 1-continued

| Comp'd No. | Property Melting point (recrystallization solvent) | NMR*1 (δ ppm/270 MHz) | IR*2 (cm$^{-1}$) | Yield (%) | Structural formula |
|---|---|---|---|---|---|
| 43 | Pale yellow crystals 103.0–105.0° C. (methanol-ethyl ether) | 1.80–2.60(10H,m), 2.98 (2H,t,J = 5.6 Hz), 3.05–3.15(2H,m), 3.29(1H,m), 3.50–3.65(4H,m), 3.60 (3H,s), 6.40(1H,d,J = 2.6 Hz), 6.70(1H,d,J = 2.6 Hz), 7.14(2H,t,J = 8.6 Hz), 7.96(2H,dd,J = 8.6 Hz, 5.3 Hz), 9.50(1H,br.s) | 3560, 2920, 1680, 1620, 1600, 1370, 1100, 970 | 41 | *(structure)* |
| 44 | Colorless prism crystals 86.0–89.0° C. (methanol) | 1.39(3H,t,J = 7.3 Hz), 1.80–2.35(8H,m), 2.49 (2H,t,J = 7.3 Hz), 2.97 (2H,t,J = 5.3 Hz), 3.05 (2H,m), 3.25(1H,m), 3.45–3.65(4H,m), 4.28(2H,q,J = 7.3 Hz), 6.41(1H,d,J = 2.6 Hz), 6.77(1H,d,J = 2.6 Hz), 7.13(2H,t,J = 8.6 Hz), 7.95(2H,dd,J = 8.6 Hz, 5.2 Hz), 9.30(1H,br.s) | 3580, 2930, 2800, 1685, 1630, 1600, 1470, 1375, 1160, 980 | 52 | *(structure)* |
| 45 | Colorless needle crystals 192.0–194.0° C. (methanol-isopropyl ether) | 1.90(2H,m), 2.48(2H,t, J = 7.6 Hz), 2.97(2H,m), 3.15–3.33(4H,m), 3.47–3.68 (4H,m), 3.86(3H,s), 6.34(1H,d,J = 3.0 Hz), 6.67(1H,d,J = 3.0 Hz), 6.85(1H,t,J = 7.3 Hz), 6.93(2H,d,J = 7.9 Hz), 7.26(2H,t,J = 7.9 Hz), 9.51(1H,br.s) | (KBr) 2822, 1636, 1599, 1470, 1436, 1240, 1156, 1002, 952 | 96 | *(structure)* |
| 46 | Colorless oil | 1.89(2H,m), 2.49(2H,t,J = 7.2 Hz), 2.55–2.75(4H,m), 2.90(2H,t,J = 5.3 Hz), 3.10–3.35(4H,m), 3.45–3.65(4H,m), 3.87(3H,s), 3.94 (3H,s), 6.42(1H,d,J = 2.6 Hz), 6.69(1H,d,J = 2.6 Hz), 6.86(1H, t,J = 7.3 Hz), 6.92(2H,d,J = 7.3 Hz), 7.26(2H,t,J = 7.3 Hz) | 2940, 2810, 1620, 1600, 1470, 1430, 1375, 1100, 1040 | 63 | *(structure)* |

TABLE 1-continued

| Comp'd No. | Property Melting point (recrystallization solvent) | NMR*1 (δ ppm/270 MHz) | IR*2 (cm⁻¹) | Yield (%) | Structural formula |
|---|---|---|---|---|---|
| 47 | Colorless needle crystals 160.0–163.0° C. (methanol) | 1.37(3H,t,J = 7.3 Hz), 1.90(2H,m), 2.48(2H,t,J = 7.3 Hz), 2.50–2.75 (4H,m), 2.93(2H,m), 3.05–3.35 (4H,m), 3.40–3.60(4H,m), 4.26 (2H,q,J = 7.3 Hz), 6.35(1H,d,J = 2.6 Hz), 6.72(1H,d,J = 2.6 Hz), 6.84(1H,t, J = 7.3 Hz), 6.92(2H,d,J = 7.3 Hz), 7.25(2H,m), 10.50(1H,br.s) | 3570, 2940, 2820, 1625, 1600, 1470, 1155, 1000, 900 | 96 | (N-C₂H₅ pyrrole-fused azepinone with NOH, N-(CH₂)₃-piperazine-N-phenyl) |
| 48 | Colorless prism crystals 180.0–181.0° C. (ethanol-isopropyl ether) | 1.80(2H,m), 2.37(2H,m), 2.50–2.68 (4H,m), 2.93(2H,m), 3.15–3.30 (4H,m), 3.40–3.60(4H,m), 5.51 (2H,s), 6.38(1H,d,J = 3.0 Hz), 6.76 (1H,d,J = 3.0 Hz), 6.85(1H,t,J = 7.3 Hz), 6.92(1H,d,J = 7.9 Hz), 7.08(2H,m), 7.17–7.35(6H,m), 9.84(1H,br.s) | (Nujol) 1615, 1600, 1500, 1470, 1245, 1230, 1000 | quant | (N-CH₂Ph pyrrole-fused azepinone with NOH, N-(CH₂)₃-piperazine-N-phenyl) |
| 49 | Colorless needle crystals 119.0–121.0° C. (methanol-ethyl ether) | 1.95(2H,m), 2.57(2H,t, J = 7.3 Hz), 2.65–2.85 (4H,m), 2.98(2H,t,J = 5.3 Hz), 3.05–3.25(4H,m), 3.50–3.65(4H,m), 3.86 (3H,s), 3.87(3H,s), 6.38(1H,d,J = 2.6 Hz), 6.69(1H,d,J = 2.6 Hz), 6.80–7.05(4H,m), 8.65(1H,br.s) | 3560, 2820, 2820, 1620, 1495, 1465, 1370, 1105, 1020, 1000, 900 | 99 | (N-CH₃ pyrrole-fused azepinone with NOH, N-(CH₂)₃-piperazine-N-(2-OCH₃-phenyl)) |
| 50 | Colorless prism crystals 150.0–152.0° C. (methanol) | 1.90(2H,m), 2.48(2H,t, J = 7.3 Hz), 2.55–2.70 (4H,m), 2.95(2H,t,J = 5.3 Hz), 3.15–3.30(4H,m), 3.45–3.65(4H,m), 3.78 (3H,s), 3.85(3H,s), 6.34(1H,d, J = 2.6 Hz), 6.41(1H,dd,J = 7.9 Hz, 1.9 Hz), 6.47(1H,t,J = 1.9 Hz), 6.53(1H,dd,J = 7.9 Hz, 1.9 Hz), 6.65(1H,d,J = 2.6 Hz), 7.16(1H,t,J = 7.9 Hz), 10.28(1H,br.s) | 3580, 2950, 2840, 1615, 1480, 1440, 1380, 1165, 1000, 965, 910 | 96 | (N-CH₃ pyrrole-fused azepinone with NOH, N-(CH₂)₃-piperazine-N-(3-OCH₃-phenyl)) |

| Comp'd No. | Property Melting point (recrystallization solvent) | NMR*1 (δ ppm/270 MHz) | IR*2 (cm$^{-1}$) | Yield (%) | Structural formula |
|---|---|---|---|---|---|
| 51 | Colorless needle crystals 175.0–176.0° C. (methanol) | 1.91(2H,m), 2.50(2H,t,J = 7.3 Hz), 2.60–2.75(4H,m), 2.96(2H,t, J = 5.9 Hz), 3.05–3.20(4H,m), 3.45–3.75(4H,m), 3.76(3H,s), 3.86(3H,s), 6.35(1H,d,J = 2.6 Hz), 6.66(1H,d,J = 2.6 Hz), 6.83(2H,d, J = 9.3 Hz), 6.91(2H,d,J = 9.3 Hz), 10.10(1H,br.s) | 3570, 2940, 2820, 1620, 1500, 1470, 1000, 905 | 94 | (structure with NOH, N-CH₃ pyrrole, N-(CH₂)₃N-piperazine-C₆H₄-OCH₃) |
| 52 | Colorless needle crystals 108.0–112.0° C. (methanol-ethyl ether) | 1.80–2.30(8H,m), 2.45–2.65(3H,m), 3.03(2H,t,J = 5.3 Hz), 3.10–3.25 (2H,m), 3.50–3.65(4H,m), 3.88(3H,s), 6.42(1H,d,J = 7.2 Hz), 6.70(1H,d,J = 2.7 Hz), 7.15–7.30 (5H,m), 9.20(1H,br.s) | 3570, 2920, 1620, 1470, 1425, 1370, 1100, 1000, 960, 900 | 99 | (structure with NOH, N-CH₃ pyrrole, N-(CH₂)₃N-piperidine-C₆H₅) |
| 53 | Colorless prism crystals 161.0–162.0° C. (methanol) | 1.50–2.10(8H,m), 2.17(2H,m), 2.40–2.65(3H,m), 2.95(2H,t, J = 5.3 Hz), 3.16(2H,m), 3.45–3.65(4H,m), 3.87(3H,s), 6.38(1H,d,J = 2.6 Hz), 6.69(1H, d,J = 2.6 Hz), 7.10–7.40(5H,m), 8.70(1H,br.s) | 3570, 2930, 1620, 1470, 1430, 1375, 1105, 995, 900 | 64 | (structure with NOH, N-CH₃ pyrrole, N-(CH₂)₄N-piperidine-C₆H₅) |
| 54 | Pale yellow prism crystals 193.0–194.0° C. (methanol) | 1.50–1.80(4H,m), 2.51(2H,t, J = 7.3 Hz), 2.50–2.80(4H,m), 2.94(2H,t,J = 5.2 Hz), 3.10–3.35 (4H,m), 3.40–3.65(4H,m), 3.87(3H,s), 6.36(1H,d,J = 2.6 Hz), 6.68(1H,d,J = 2.6 Hz), 6.86(1H,t, J = 7.2 Hz), 6.92(2H,d,J = 7.2 Hz), 7.26(2H,t,J = 7.2 Hz), 8.80(1H,br.s) | 3570, 2930, 2820, 1620, 1600, 1470, 1430, 1370, 1120, 990, 900 | 73 | (structure with NOH, N-CH₃ pyrrole, N-(CH₂)₄N-piperazine-C₆H₅) |

TABLE 1-continued

TABLE 1-continued

| Comp'd No. | Property Melting point (recrystallization solvent) | NMR*1 (δ ppm/270 MHz) | IR*2 (cm⁻¹) | Yield (%) | Structural formula |
|---|---|---|---|---|---|
| 55 | Colorless powdery crystals 197.5–198.0° C. (ethanol) | 1.89(2H,m), 2.38–2.57(6H,m), 2.98(2H,m), 3.50–3.62 (4H,m), 3.84(4H,m), 3.88(3H,s), 6.38(1H,d,J = 3.3 Hz), 6.48(1H,m), 6.70(1H,d,J = 3.3 Hz), 7.72(1H,br.s), 8.30(2H,d,J = 4.6 Hz) | (KBr) 3240, 1583, 1544, 1503, 1488, 1442, 1360, 1312, 1267, 1256, 982, 965, 916, 803, 784 | 96 | (structure with pyrimidinyl-piperazine) |
| 56 | Colorless prism crystals 167.5–169.5° C. (ethanol) | 1.89(2H,quint,J = 7.3 Hz), 2.48(2H,t,J = 7.3 Hz), 2.65 (4H,m), 2.98(2H,m), 3.58 (4H,m), 3.87(3H,s), 6.33 (1H,d, J = 2.6 Hz), 6.67(1H,d, J = 2.6 Hz), 6.82–7.03(4H,m), 9.54(1H,br.s) | (KBr) 3248, 1597, 1508, 1472, 1433, 1239, 1158, 928, 819, 783 | 98 | (structure with 4-fluorophenyl-piperazine, N-CH₃) |
| 57 | Colorless prism crystals 150.5–151.5° C. (ethanol) | 1.39(3H,t,J = 7.3 Hz), 1.89 (2H,m), 2.48(2H,t,J = 7.3 Hz), 2.64(4H,m), 2.97(2H,m), 3.16(4H,m), 3.43–3.68(4H,m), 4.29(2H,t,J = 7.3 Hz), 6.35(1H, d,J = 3.0 Hz), 6.76(1H,d,J = 3.0 Hz), 6.81–7.04(4H,m), 9.13(1H,br.s) | (KBr) 2940, 2830, 1630, 1510, 1475, 1440, 1370, 1235, 1160, 1010, 970, 925 | 91 | (structure with 4-fluorophenyl-piperazine, N-C₂H₅) |
| 58 | Pale yellow oil | 1.87(4H,m), 2.02(2H,m), 2.33 (2H,m), 2.44(2H,m), 2.76(2H,m), 2.99(2H,m), 3.50–3.63(4H,m), 3.87(3H,s), 4.24(1H,m), 6.39(1H,d,J = 2.6 Hz), 6.69(1H, d,J = 2.6 Hz), 6.84(2H,m), 6.95(2H,m), 8.75(1H,br.s) | (film) 1624, 1504, 1477, 1434, 1372, 1248, 1206, 1044, 1004, 963, 829, 763 | 98 | (structure with 4-fluorophenoxy-piperidine, N-CH₃) |

TABLE 1-continued

| Comp'd No. | Property Melting point (recrystallization solvent) | NMR*1 (δ ppm/270 MHz) | IR*2 (cm⁻¹) | Yield (%) | Structural formula |
|---|---|---|---|---|---|
| 59 | Pale yellow oil | 1.49–1.98(6H,m), 2.06(2H,m), 2.38(2H,m), 2.80–3.06(5H,m), 3.54(4H,m), 3.86(3H,s), 6.42 (1H,d,J = 2.6 Hz), 6.69(1H,d,J = 2.6 Hz), 6.99(2H,dt,J = 2.0 Hz, 9.2 Hz), 7.40(1H,dd,J = 2.6 Hz,9.2 Hz), 7.42(1H,dd,J = 2.6 Hz,9.2 Hz), 9.15(1H,br.s) | (film) 1624, 1489, 1431, 1374, 1248, 1220, 1155, 1003, 776, 754 | 99 | |
| 60 | Colorless prism crystals 155.0–156.0° C. (methanol-ethyl ether) | 1.53–1.90(4H,m), 2.01 (2H,m), 2.66(1H,m), 2.75–2.95(2H,m), 2.97(2H,t, J = 5.3 Hz), 3.56(2H,t,J = 5.3 Hz), 3.61(2H,t,J = 7.2 Hz), 3.87(3H,s), 4.19(2H,t,J = 7.2 Hz), 4.20–4.35(2H,m), 6.38 (1H,d,J = 2.6 Hz), 6.68 (1H,d,J = 2.6 Hz), 7.10–7.35(5H,m), 7.50(1H,br.s) | 3570, 2940, 1690, 1630, 1470, 1430, 1280, 1110 | 99 | |
| 61 | Colorless oil | 2.01(2H,t,J = 7.2 Hz), 2.98 (2H,t,J = 5.3 Hz), 3.00–3.15 (4H,m), 3.57(2H,t,J = 5.3 Hz), 3.62(2H,t,J = 7.2 Hz), 3.65–3.80(4H,m), 3.87(3H,s), 3.88(3H,s), 4.20(2H,t, J = 7.2 Hz), 6.38(1H,d,J = 2.7 Hz), 6.70(1H,d,J = 2.7 Hz), 6.85–7.10(4H,m), 8.80(1H,br.s) | 3560, 2960, 1690, 1620, 1500, 1470, 1420, 1100 | 91 | |

TABLE 1-continued

| Comp'd No. | Property Melting point (recrystallization solvent) | NMR*1 (δ ppm/270 MHz) | IR*2 (cm$^{-1}$) | Yield (%) | Structural formula |
|---|---|---|---|---|---|
| 62 | Colorless needle crystals 176.0–176.5° C. (methanol) | 2.01(2H,tt,J = 7.6 Hz, 7.3 Hz), 2.98(2H,t,J = 5.3 Hz), 3.10–3.25(4H,m), 3.57(2H,t,J = 5.3 Hz), 3.60–3.80(m), 3.63(t,J = 7.3 Hz), (6H in total), 3.87(3H,s), 4.20(2H,t,J = 6.6 Hz), 6.38(1H,d,J = 2.7 Hz), 6.70(1H,d,J = 2.7 Hz), 6.97(1H,t,J = 7.3 Hz), 7.06(2H,d,J = 7.3 Hz), 7.30(2H,t,J = 7.3 Hz), 9.30(1H,br.s) | 3570, 2930, 1690, 1620, 1600, 1470, 1420, 1120, 990 | 96 | (structure shown) |

*1: Measured in CDCl$_3$ with TMS as an internal standard.
*2: Measured as a CHCl$_3$ solution unless otherwise specifically indicated.

Test

With respect to the compounds of the present invention, their anti-$\alpha_1$ action and anti-serotonin (5-HT) action were investigated by the testing methods which will be described below. The test results of some representative compounds are tabulated below.

(1) Anti-$\alpha_1$ action

The thoracic aorta of each Hartley male guinea pig (body weight: 300–500 g) was excised. A sample cut in a helical form was suspended under 1 g load in a Magnus cylinder filled with the Tyrode solution of 37° C. which had been saturated with a mixed gas consisting of 95% $O_2$+5% $CO_2$. Using an isometric transducer ("TB-612J"/NIHON KOHDEN) and a pressure preamplifier ("AP-620G"/NIHON KOHDEN), variations in tension were measured. The measurement results were recorded on a thermal pen-writing recorder ("WT-647G"/NIHON KOHDEN).

Taking the tonic contraction induced by $10^{-5}$M norepinephrine (NE) as 100%, the percent contractions upon addition of each test drug at $10^{-8}$ and $10^{-7}$M were determined as anti-$\alpha_1$ action.

(2) Anti-serotonin action (anti-5-HT action)

The superior mesenteric artery of each Hartley male guinea pig (body weight: 300–500 g) was excised. A sample cut in a helical form was suspended under 0.3 g load in a Magnus cylinder filled with the Tyrode solution of 37° C. which had been saturated with a mixed gas consisting of 95% $O_2$+5% $CO_2$. Using an isometric transducer ("UL-10"/SHINKOH K.K.) and a pressure preamplifier ("DSA-605A"/SHINKOH K.K.), variations in tension were measured. The measurement results were recorded on a pen-writing recorder ("VP-6537A"/NATIONAL K.K.). Taking the contraction induced by $10^{-5}$M serotonin (5-HT) as 100%, the percent contractions induced by $10^{-5}$M 5-HT in the presence of each test drug at $10^{-7}$ and $10^{-6}$M were determined as anti-5-HT action.

(Results)

| Comp'd No. | Anti $\alpha_1$ action (% of Control) | | Anti 5-HT action (% of Control) | |
|---|---|---|---|---|
| | $10^{-8}$ M | $10^{-7}$ M | $10^{-7}$ M | $10^{-6}$ M |
| 18* | 100.0 | 85.5 | 52.8 | 16.3 |
| 19* | 100.0 | 90.1 | 60.3 | 12.4 |
| 39 | 99.3 | 80.5 | 34.3 | 8.7 |
| 40 | 100.0 | 94.5 | 24.2 | 12.5 |
| 43 | 73.3 | 37.9 | 43.1 | 8.7 |
| 45 | 79.8 | 23.8 | 11.2 | — |
| 46 | 78.7 | 28.0 | 59.5 | 12.8 |
| 47 | 100.0 | 81.9 | 5.2 | — |
| 48 | 98.9 | 60.5 | 52.8 | 5.1 |
| 50 | 57.6 | 38.8 | 60.0 | 18.4 |
| 52 | 97.2 | 62.6 | 39.1 | 9.9 |

*The test compound was obtained by converting the compound to its hydrochloride with excess hydrogen chloride in an organic solvent and, if necessary, subjecting the hydrochloride to recrystallization.

(3) Anti-platelet-aggregating action

Blood was drawn from the auricular artery of Japanese white house rabbit (male, about 3 kg), whereby a platelet rich plasma sample (PRP) was prepared. Platelet aggregating ability was measured using a platelet aggregation measuring apparatus ("PAM-SC"/MEBANIX).

Found under the presence of 1 mM of $CaCl_2$ was a controlling action of the test drug ($10^{-7}$M) against the maximum reaction (100%) of the platelet aggregation induced by $10^{-6}$M of ADP+$10^{-5}$M of 5-HT.

(Results)

| Compound No. | Inhibitory rate of platelet aggregation (%) |
|---|---|
| 39 | 33 |
| 43 | 18 |
| 45* | 30 |
| 47 | 34 |
| Ketanserin tartrate | 20 |

*The test compound was obtained by converting the compound to its hydrochloride with excess hydrogen chloride in an organic solvent and, if necessary, subjecting the hydrochloride to recrystallization.

Industrial Applicability

The pyrroloazepine compounds according to the present invention are drugs having excellent antiserotonin action. Coupled with their high safety, they can therefore be used as novel therapeutics for ischemic heart diseases.

Particularly, these compounds according to the present invention include those having strong anti-$\alpha_1$ action in addition to the excellent antiserotonin action. Such compounds are effective as hypotensive drugs. Pyrroloazepine compounds according to the present invention are therefore useful as therapeutics for various circulatory diseases.

We claim:

1. A pyrroloazepine compound represented by the following formula (I) or (II):

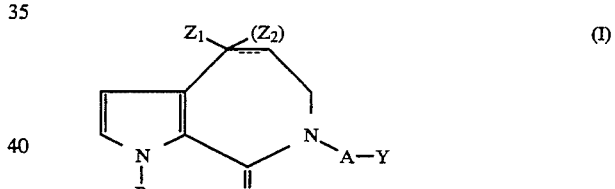

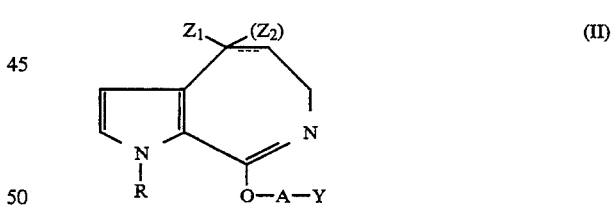

wherein the dashed line indicates the presence or absence of a bond and when the bond indicated by the dashed line is present, $Z_1$ represents a hydrogen atom but, when the bond indicated by the dashed line is absent, $Z_1$ represents a hydrogen atom and $Z_2$ represents a hydroxyl group or $Z_1$ and $Z_2$ are taken together to form an oxygen atom or a group $NOR_1$, in which $R_1$ represents a hydrogen atom, an alkyl group, a substituted or unsubstituted aryl group or a substituted or unsubstituted aralkyl group; R represents an alkyl group, a cycloalkyl group, a cycloalkyl-alkyl group, a substituted or unsubstituted aryl group, or a substituted or unsubstituted aralkyl group; A represents an alkylene, alkenylene or alkynylene group; and Y represents a substituted or un- substituted heterocyclic group or a group:

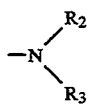

in which R₂ and R₃ may be the same or different and individually represent a hydrogen atom, an alkyl group (which may be substituted by a lower alkoxy group or a substituted or unsubstituted aryloxy group), a substituted or unsubstituted aryl group or a substituted or unsubstituted aralkyl group; or a salt thereof.

2. A pyrroloazepine compound or a salt thereof according to claim 1, wherein in the formula (I) or (II), Y represents a heterocyclic group represented by the following formula:

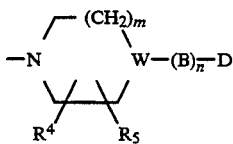

in which R₄ and R₅ may be the same or different and individually represent a hydrogen atom or an alkyl group; W represents a group C—R₆ or a nitrogen atom, in which R₆ represents a hydrogen atom or an alkyl group, and when W represents C—R₆, m stands for 0, 1 or 2, B represents an oxygen atom, a sulfur atom, a carbonyl group, a sulfinyl group, a sulfonyl group, an alkylene group, an alkenylene group, a substituted or unsubstituted phenylmethylene group, a substituted or unsubstituted hydroxymethylene group or a substituted or unsubstituted, cyclic or noncyclic acetal group but, when W represents a nitrogen atom, m stands for 1 or 2, B represents a carbonyl group, a sulfonyl group, an alkylene group, an alkenylene group or a substituted or unsubstituted phenylmethylene group; n stands for 0 or 1; and D represents a substituted or unsubstituted aryl group or substituted or unsubstituted aromatic heterocyclic group.

3. A pyrroloazepine compound or a salt thereof according to claim 1, wherein in the formula (I) or (II), Z₁ and Z₂ are taken together to form an oxygen atom or a group NOR₁, in which R₁ has the same meaning as defined above.

4. A pyrroloazepine compound or a salt thereof according to claim 1, wherein in the formula (I) or (II), Y represents a substituted or unsubstituted piperidinyl or piperazinyl group.

5. A process for the preparation of a pyrroloazepine compound represented by the following formula (Ia) or (IIa):

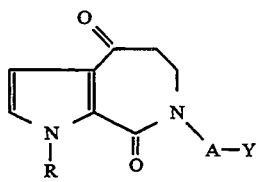

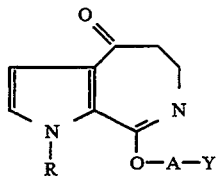

wherein A, R and Y have the same meanings as defined in claim 1, which comprises:
reacting a compound represented by the following formula (III):

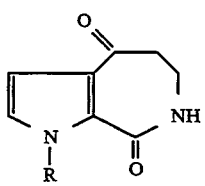

wherein R has the same meaning as defined above with a compound represented by the following formula (IV):

wherein A has the same meanings as defined above and X and X' may be the same or different and individually mean a substituent easily replaceable with an amino group, thereby obtaining a compound represented by the following formula (V):

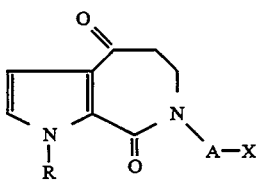

wherein A, R and X have the same meanings as defined above; and then
reacting the compound of the formula (V) with a nitrogen-containing compound represented by the following formula (VI):

wherein Y has the same meaning as defined above.

6. A process for the preparation of a pyrroloazepine compound represented by the following formula (Ia):

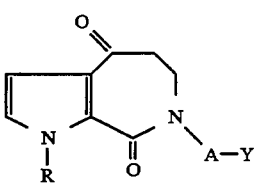

wherein A, R and Y have the same meanings as defined in claim 1, which comprises reacting a compound represented by the following formula (III):

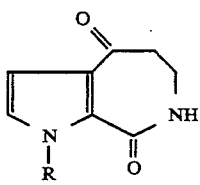 (III)
wherein R has the same meaning as defined above with a compound represented by the following formula (VII):
$$X-AY \qquad \text{(VII)}$$
wherein A, X and Y have the same meanings as defined above.
7. A therapeutic for circulatory diseases, comprising as an active ingredient a pyrroloazepine derivative (I) or (II) or a salt thereof as described in claim 1.
* * * * *